(12) United States Patent
Quon et al.

(10) Patent No.: US 8,735,548 B2
(45) Date of Patent: May 27, 2014

(54) ANTIBODIES WHICH BIND TO SCNN1A/TNFRSF1A FUSION PROTEINS AND METHODS OF USE THEREOF

(75) Inventors: Kim Coign Quon, Seattle, WA (US); Gene Cutler, San Francisco, CA (US); Jennifer Joy Kordich, Sammamish, WA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/805,321

(22) PCT Filed: Jun. 28, 2011

(86) PCT No.: PCT/US2011/042201
§ 371 (c)(1),
(2), (4) Date: Jan. 4, 2013

(87) PCT Pub. No.: WO2012/012141
PCT Pub. Date: Jan. 26, 2012

(65) Prior Publication Data
US 2013/0095111 A1   Apr. 18, 2013

Related U.S. Application Data

(60) Provisional application No. 61/501,080, filed on Jun. 24, 2011, provisional application No. 61/360,381, filed on Jun. 30, 2010.

(51) Int. Cl.
*C12P 21/08* (2006.01)
*C07K 16/00* (2006.01)
*G01N 33/574* (2006.01)

(52) U.S. Cl.
USPC .......... 530/387.3; 530/387.9; 530/391.7; 435/7.23

(58) Field of Classification Search
None
See application file for complete search history.

(56) References Cited

U.S. PATENT DOCUMENTS 6,703,204 B1 *   3/2004   Mutter et al. ............... 435/6.17

FOREIGN PATENT DOCUMENTS

WO   02/092854 A2   11/2002
WO   2008/093323 A2   8/2008

OTHER PUBLICATIONS

Stanke F, et al. Hum. Genet. 119:331-343, Apr. 2006. Available online at DOI 10.1007/s00439-006-0140-2.*
Christen, U. et al., "Immune response to a recombinant human TNFR55-IgG1 fusion protein: Auto-antibodies in rheumatoid arthritis (RA) and multiple sclerosis (MS) patients have neither neutralizing nor agonist activities." *Human Immunology* 60(9): 774-790, Sep. 1999.
Del Monaco, S. et al., "Epithelial sodium channel in a human trophoblast cell line (BeWo)." *J. of Membrane Biology* 223(3):127-139, Jun. 2008.
Stanke, F. et al., "The TNF alpha receptor TNFRSF1A and genes encoding the amiloride-sensitive sodium channel ENaC as modulators in cystic fibrosis."*Human Genetics* 119(3): 331-343, Apr. 2006.
Kimura, K. et al., "Diversification of transcriptional modulation: Large-scale identification and characterization of putative alternative promoters of human genes," *Genome Research* 16:55-65, 2006.
Accession No. DA950392 from Kimura et al., (D4), 2006.

* cited by examiner

*Primary Examiner* — Robert Landsman
(74) *Attorney, Agent, or Firm* — Julie K. Smith

(57) ABSTRACT

The present invention provides fusion proteins expressed by cancer cells, antibodies and other antigen-binding agents that specifically bind to the fusion proteins, and compositions and methods for using the antibodies and other antigen-binding agents to detect, characterize, and treat cancer.

17 Claims, 2 Drawing Sheets

ANTIBODIES WHICH BIND TO SCNN1A/TNFRSF1A FUSION PROTEINS AND METHODS OF USE THEREOF

CROSS-REFERENCE TO RELATED APPLICATIONS

The application is a national stage application under 35 U.S.C. §371 of International Application No. PCT/US2011/042201, having an international filing date of Jun. 28, 2011; which claims priority to U.S. patent application Ser. No. 61/360,381 filed Jun. 30, 2010 and U.S. patent application Ser. No. 61/501,080 filed Jun. 24, 2011, which are incorporated herein by reference.

REFERENCE TO THE SEQUENCE LISTING

The present application is being filed along with a Sequence Listing in electronic format. The Sequence Listing is provided as a file entitled A-1587-US-PCT_SeqListingfiled121812.txt, created Dec. 18, 2012, which is 52 KB in size. The information in the electronic format of the Sequence Listing is incorporated herein by reference in its entirety.

FIELD OF THE INVENTION

This invention relates to novel fusion proteins expressed by ovarian and other cancer cells, and to compositions and methods for detecting, characterizing, and treating ovarian and other cancers.

BACKGROUND OF THE INVENTION

Cancer is the second-leading cause of death in the U.S. In 2011, the American Cancer Society projects 1,596,670 new cancer cases and 571,950 deaths from cancer. Ovarian cancer is the ninth most common cancer in women and the fifth most common cause of cancer death in women in the U.S. Ovarian cancer includes those tumors that arise from various tissue types of the ovary. Tumors are classified according to the cell type from which they originate, including three main types of tumors: epithelial tumors (including the most common serous subtype), germ cell tumors, and stromal cell tumors. Ovarian cancer is difficult to diagnose at an early stage due to its non-specific symptoms and rapid rate of metastasis. The majority of ovarian cancer cases are therefore diagnosed at a late stage, leading to low survival rates. There is a high unmet need for better methods of detecting and treating ovarian cancer, as well as lung, bladder, thyroid, and other tumor types.

SUMMARY OF THE INVENTION

The present invention provides novel fusion proteins, including fusion junction peptides that are overexpressed by ovarian cancer cells and other cancer cells as compared to normal cells. The invention provides the fusion proteins SEQ ID NO: 4 and SEQ ID NO: 6 as well as fragments thereof.

In some embodiments the fusion proteins comprise polypeptide fragments including a 12/2 form of the junction peptide, e.g. comprising amino acids 539-548 of SEQ ID NO: 4, amino acids 535-553 of SEQ ID NO: 4, amino acids 530-559 of SEQ ID NO: 4, amino acids 524-563 of SEQ ID NO: 4, or larger fragments of SEQ ID NO: 4 including amino acids 535-553 of SEQ ID NO: 4. In some embodiments the fusion proteins comprise polypeptide fragments including a 12/2 form of the junction peptide, e.g. comprising amino acids 391-548 of SEQ ID NO: 4, amino acids 386-548 of SEQ ID NO: 4, amino acids 381-548 of SEQ ID NO: 4, or larger fragments of SEQ ID NO: 4 including amino acids 391-548 of SEQ ID NO: 4.

Some aspects of the invention provide a contiguous fragment of SEQ ID NO: 4 including at least amino acids x-553, wherein in some embodiments x is a residue selected from amino acids 1-391 and in some embodiments x is a residue selected from amino acids 108-391. In some embodiments the fusion proteins comprise amino acids 108-741 of SEQ ID NO: 4.

In some embodiments the fusion proteins comprise polypeptide fragments including a 13/2 form of the junction peptide, e.g. comprising amino acids 600-609 of SEQ ID NO: 6, amino acids 596-614 of SEQ ID NO: 6, amino acids 591-620 of SEQ ID NO: 6, amino acids 585-624 of SEQ ID NO: 6, or larger fragments of SEQ ID NO: 6 including amino acids 596-614 of SEQ ID NO: 6. In some embodiments the fusion proteins comprise amino acids 108-802 of SEQ ID NO: 6.

In some embodiments the fusion protein fragments consist of amino acids 539-548 of SEQ ID NO: 4, amino acids 535-553 of SEQ ID NO: 4, amino acids 530-559 of SEQ ID NO: 4, amino acids 524-563 of SEQ ID NO: 4, amino acids 391-548 of SEQ ID NO: 4, amino acids 386-548 of SEQ ID NO: 4, amino acids 381-548 of SEQ ID NO: 4, amino acids 108-741 of SEQ ID NO: 4, amino acids 600-609 of SEQ ID NO: 6, amino acids 596-614 of SEQ ID NO: 6, amino acids 591-620 of SEQ ID NO: 6, amino acids 585-624 of SEQ ID NO: 6, or amino acids 108-802 of SEQ ID NO: 6.

The present invention provides nucleic acids encoding the novel fusion proteins, fragments thereof, and also probes and primers used to amplify and detect nucleic acids encoding the novel fusion proteins. The nucleic acids may be double stranded or single stranded, the nucleic acids may be DNA, RNA, or artificial variants thereof. In some embodiments the nucleic acids encode polypeptides comprising or consisting of SEQ ID NO: 4 or SEQ ID NO: 6.

In some embodiments the nucleic acids encode polypeptides comprising amino acids 539-548 of SEQ ID NO: 4, amino acids 535-553 of SEQ ID NO: 4, amino acids 530-559 of SEQ ID NO: 4, amino acids 524-563 of SEQ ID NO: 4, amino acids 391-548 of SEQ ID NO: 4, amino acids 386-548 of SEQ ID NO: 4, amino acids 381-548 of SEQ ID NO: 4, amino acids 108-741 of SEQ ID NO: 4, amino acids 600-609 of SEQ ID NO: 6, amino acids 596-614 of SEQ ID NO: 6, amino acids 591-620 of SEQ ID NO: 6, amino acids 585-624 of SEQ ID NO: 6, or amino acids 108-802 of SEQ ID NO: 6. In some embodiments the nucleic acids encode polypeptides consisting of SEQ ID No: 4 or SEQ ID NO: 6.

In some embodiments the nucleic acids encode polypeptides consisting of amino acids 539-548 of SEQ ID NO: 4, amino acids 535-553 of SEQ ID NO: 4, amino acids 530-559 of SEQ ID NO: 4, amino acids 524-563 of SEQ ID NO: 4, amino acids 391-548 of SEQ ID NO: 4, amino acids 386-548 of SEQ ID NO: 4, amino acids 381-548 of SEQ ID NO: 4, amino acids 108-741 of SEQ ID NO: 4, amino acids 600-609 of SEQ ID NO: 6, amino acids 596-614 of SEQ ID NO: 6, amino acids 591-620 of SEQ ID NO: 6, amino acids 585-624 of SEQ ID NO: 6, or amino acids 108-802 of SEQ ID NO: 6.

Some aspects of the invention provide a nucleic acid encoding a contiguous fragment of SEQ ID NO: 4 including at least amino acids x-553, wherein in some embodiments x is a residue selected from amino acids 1-391 and in some embodiments x is a residue selected from amino acids 108-391.

Some aspects of the invention provide primer pairs for amplifying nucleic acids encoding the 12/2 or 13/2 junction, e.g. the primer pair SEQ ID NO: 7 and SEQ ID NO: 8 or the primer pair SEQ ID NO: 10 and SEQ ID NO: 11. The primers can be any length, for example, 15, 20, 25, 30, or more nucleotides in length, in which one member of the primer pair hybridizes to a nucleic acid encoding the SCNN1A portion of the fusion sequence and one member of the primer pair hybridizes to a nucleic acid encoding the TNFRSF1A portion of the fusion sequence. Some aspects of the invention provide probes for detecting nucleic acids encoding the 12/2 or 13/2 fusion junction, e.g. SEQ ID NO: 9 or SEQ ID NO: 12. In some embodiments the probes are labeled with a fluorescent or isotope label. The probes can be any length, for example, 15, 20, 25, 30, or more nucleotides in length, in which the probe recognizes the SCNN1A 12/2 TNFRSF1A fusion junction or the 13/2 TNFRSF1A fusion junction.

Also provided are vectors comprising the nucleic acids of the invention. In one embodiment the vector is an expression vector. Also provided is a host cell comprising the vector.

The invention provides recombinant host cells that express the 12/2 or 13/2 fusion proteins or fragments thereof on the cell surface.

In some embodiments the invention provides antigen-binding agents including antibodies that specifically bind to the fusion junction peptides and fusion proteins, the antigen binding agents preferably having a greater affinity for the fusion proteins than for either of the fusion partners that make up the fusion protein.

The antibodies of the invention may be monoclonal or polyclonal antibodies. In some embodiments the antibodies are chimeric, humanized, or human antibodies. In some embodiments the antibodies are single chain antibodies or Fab fragments.

In some aspects the invention provides an isolated antigen binding agent that specifically binds to a SCNN1A/TNFRSF1A fusion protein. In some preferred embodiments the binding agent is a monoclonal antibody. In some aspects the invention provides an isolated monoclonal antibody or other antigen binding agent that specifically binds to a SCNN1A/TNFRSF1A fusion protein, wherein the antigen binding agent specifically binds to a SCNN1A/TNFRSF1A fusion protein selected from: (a) SEQ ID NO: 4, or a fragment thereof comprising the sequence SEQ ID NO: 1, and (b) SEQ ID NO: 6, or a fragment thereof comprising the sequence SEQ ID NO: 2.

In some aspects the invention provides a monoclonal antibody wherein the antibody binds a SCNN1A/TNFRSF1A fusion protein with an affinity less than 1 nM and specifically binds a SCNN1A/TNFRSF1A fusion protein with at least 100-fold higher affinity than it binds either SCNN1A or TNFRSF1A.

In some aspects the monoclonal antibody or other isolated binding agent specifically binds a fusion protein consisting of amino acids 539-548 of SEQ ID NO: 4, amino acids 535-553 of SEQ ID NO: 4, amino acids 530-559 of SEQ ID NO: 4, amino acids 524-563 of SEQ ID NO: 4, amino acids 391-548 of SEQ ID NO: 4, amino acids 386-548 of SEQ ID NO: 4, amino acids 381-548 of SEQ ID NO: 4, amino acids 108-741 of SEQ ID NO: 4, amino acids 600-609 of SEQ ID NO: 6, amino acids 596-614 of SEQ ID NO: 6, amino acids 591-620 of SEQ ID NO: 6, amino acids 585-624 of SEQ ID NO: 6, or amino acids 108-802 of SEQ ID NO: 6.

Some aspects of the invention provide an antibody or other binding agent that specifically binds a fragment of SEQ ID NO: 4 including at least amino acids x-553, wherein in some embodiments x is a residue selected from amino acids 1-391 and in some embodiments x is a residue selected from amino acids 108-391.

In some embodiments the antibody or other binding agent specifically binds to the fusion proteins SEQ ID NO: 4, SEQ ID NO: 6, or to fragments thereof, expressed on the surface of a recombinant cell.

Also provided is a hybridoma capable of producing the antibodies of the present invention. Also provided is a method of making the antibodies or other antigen binding agents comprising culturing a host cell under conditions that allow it to express the antigen binding agent.

The invention provides methods of making antibodies that can be used for detecting, characterizing, and treating tumors comprising immunizing an animal with a polypeptide selected from SEQ ID NO: 4 or a fragment thereof comprising the sequence SEQ ID NO: 1, SEQ ID NO: 6 or a fragment thereof comprising the sequence SEQ ID NO: 2, amino acids 539-548 of SEQ ID NO: 4, amino acids 535-553 of SEQ ID NO: 4, amino acids 530-559 of SEQ ID NO: 4, amino acids 524-563 of SEQ ID NO: 4, amino acids 391-548 of SEQ ID NO: 4, amino acids 386-548 of SEQ ID NO: 4, amino acids 381-548 of SEQ ID NO: 4, amino acids 108-741 of SEQ ID NO: 4, amino acids 600-609 of SEQ ID NO: 6, amino acids 596-614 of SEQ ID NO: 6, amino acids 591-620 of SEQ ID NO: 6, amino acids 585-624 of SEQ ID NO: 6, and amino acids 108-802 of SEQ ID NO: 6. In some embodiments the polypeptide used to immunize the animal is expressed on the surface of a recombinant cell. In some embodiments the resulting antibodies are isolated using standard methods known in the art. In some embodiments the animal expresses human antibodies.

The invention provides methods of making antibodies that can be used for detecting, characterizing, and treating tumors comprising screening a library of antibodies expressed on phage, phagemids, ribosomes, or other particles with a polypeptide selected from SEQ ID NO: 4 or a fragment thereof comprising the sequence SEQ ID NO: 1, SEQ ID NO: 6 or a fragment thereof comprising the sequence SEQ ID NO: 2, amino acids 539-548 of SEQ ID NO: 4, amino acids 535-553 of SEQ ID NO: 4, amino acids 530-559 of SEQ ID NO: 4, amino acids 524-563 of SEQ ID NO: 4, amino acids 391-548 of SEQ ID NO: 4, amino acids 386-548 of SEQ ID NO: 4, amino acids 381-548 of SEQ ID NO: 4, amino acids 108-741 of SEQ ID NO: 4, amino acids 600-609 of SEQ ID NO: 6, amino acids 596-614 of SEQ ID NO: 6, amino acids 591-620 of SEQ ID NO: 6, amino acids 585-624 of SEQ ID NO: 6, and amino acids 108-802 of SEQ ID NO: 6. In some embodiments the polypeptide used to screen the library is expressed on the surface of a recombinant cell. In some embodiments the resulting antibodies are isolated using standard methods known in the art. In some embodiments the library is a library of human antibodies.

Also provided are isolated nucleic acid molecules comprising a polynucleotide sequence encoding the light chain variable domain, the heavy chain variable domain, or both, of the antibodies or other antigen binding agents of the invention. In one embodiment, the polynucleotide comprises a light chain variable sequence, and a heavy chain variable sequence.

In some aspects the invention provides bispecific antibodies or other binding agents in which one antigen-binding site binds an epitope on SCNN1A and one antigen-binding site binds an epitope on TNFRSF1A. In some aspects of the invention the bispecific binding agent is an antibody that specifically binds to a SCNN1A/TNFRSF1A fusion protein selected from: (a) SEQ ID NO: 4, or a fragment thereof comprising the sequence SEQ ID NO: 1, and (b) SEQ ID NO: 6, or a fragment thereof comprising the sequence SEQ ID NO: 2.

In some aspects the invention provides antibodies with enhanced effector functions. In other aspects the invention provides antibodies conjugated to a toxin or other therapeutic agent. In some aspects of the invention the toxin or other therapeutic agent is joined to the antibody by means of a cleavable or non-cleavable linker. In some aspects the toxin or other therapeutic agent is an auristatin or maytansinoid.

Also provided is a pharmaceutical composition comprising the antibodies or other antigen binding proteins of the present invention. In one embodiment the pharmaceutical composition comprises a human antibody.

In some embodiments the invention provides methods useful to detect and characterize ovarian, bladder, lung, thyroid, and other types of tumors. Some aspects of the invention comprise detecting expression of a fusion protein according to the invention in cells from the tumor. In some embodiments the fusion protein detected is selected from: (a) SEQ ID NO: 4, or a fragment thereof comprising the sequence SEQ ID NO: 1, and (b) SEQ ID NO: 6, or a fragment thereof comprising the sequence SEQ ID NO: 2. Some embodiments comprise detecting a polypeptide comprising amino acids 539-548 of SEQ ID NO: 4, amino acids 535-553 of SEQ ID NO: 4, amino acids 530-559 of SEQ ID NO: 4, amino acids 524-563 of SEQ ID NO: 4, amino acids 391-548 of SEQ ID NO: 4, amino acids 386-548 of SEQ ID NO: 4, amino acids 381-548 of SEQ ID NO: 4, amino acids 108-741 of SEQ ID NO: 4, amino acids 600-609 of SEQ ID NO: 6, amino acids 596-614 of SEQ ID NO: 6, amino acids 591-620 of SEQ ID NO: 6, amino acids 585-624 of SEQ ID NO: 6, or amino acids 108-802 of SEQ ID NO: 6. Some embodiments comprise detecting polypeptides consisting of amino acids 539-548 of SEQ ID NO: 4, amino acids 535-553 of SEQ ID NO: 4, amino acids 530-559 of SEQ ID NO: 4, amino acids 524-563 of SEQ ID NO: 4, amino acids 391-548 of SEQ ID NO: 4, amino acids 386-548 of SEQ ID NO: 4, amino acids 381-548 of SEQ ID NO: 4, amino acids 108-741 of SEQ ID NO: 4, amino acids 600-609 of SEQ ID NO: 6, amino acids 596-614 of SEQ ID NO: 6, amino acids 591-620 of SEQ ID NO: 6, amino acids 585-624 of SEQ ID NO: 6, or amino acids 108-802 of SEQ ID NO: 6. In some embodiments the fusion protein detected is a contiguous fragment of SEQ ID NO: 4 including at least amino acids x-553, wherein in some embodiments x is a residue selected from amino acids 1-391 and in some embodiments x is a residue selected from amino acids 108-391.

In some aspects of the invention expression of the fusion protein is detected at the level of RNA. In other aspects of the invention expression of the fusion protein is detected at the level of protein. In some aspects of the invention expression of the fusion protein is detected through the use of an antibody that specifically binds the fusion protein. The invention includes embodiments in which nucleic acids encoding the fusion proteins are amplified using a primer pair in which one member of the primer pair hybridizes to the SCNN1A portion of the fusion sequence and one member of the primer pair hybridizes to the TNFRSF1A portion of the fusion sequence. In some embodiments the primer pair comprises SEQ ID NO: 7 and SEQ ID NO: 8 or the primer pair comprises SEQ ID NO: 10 and SEQ ID NO: 11. The invention includes embodiments in which nucleic acids encoding the fusion proteins are detected using a probe for the fusion protein junction. In some embodiments the probe comprises SEQ ID NO: 9 or SEQ ID NO: 12.

In some embodiments, antibodies or other antigen binding agents of the invention are useful to treat ovarian, bladder, lung, thyroid, and other cancers or for preparing a medicament for use in treating ovarian, bladder, lung, thyroid, and other cancers. The invention includes a method of inhibiting proliferation of cells expressing a SCNN1A/TNFRSF1A fusion protein comprising contacting the cells with a composition comprising an antigen binding agent or bispecific antibody that specifically binds to a SCNN1A/TNFRSF1A fusion protein. In some aspects the antigen binding agent is an antibody according to the invention. Some aspects of the invention are directed to a method of treating a patient with cancer, comprising administering a composition comprising an antigen binding agent or bispecific antibody that specifically binds to a SCNN1A/TNFRSF1A fusion protein. Some aspects of the invention are directed to a method of preparing a medicament for use in treating a patient with cancer, comprising a composition comprising an antigen binding agent or bispecific antibody that specifically binds to a SCNN1A/TNFRSF1A fusion protein. In some aspects the antigen binding agent is an antibody according to the invention.

In some aspects of the invention a patient is treated with an antibody or other antigen binding agent that specifically binds to a SCNN1A/TNFRSF1A fusion protein selected from: (a) SEQ ID NO: 4, or a fragment thereof comprising the sequence SEQ ID NO: 1, and (b) SEQ ID NO: 6, or a fragment thereof comprising the sequence SEQ ID NO: 2.

In some embodiments a patient is treated with an antigen binding agent that specifically binds to a SCNN1A/TNFRSF1A fusion protein comprising amino acids 539-548 of SEQ ID NO: 4, amino acids 535-553 of SEQ ID NO: 4, amino acids 530-559 of SEQ ID NO: 4, amino acids 524-563 of SEQ ID NO: 4, amino acids 391-548 of SEQ ID NO: 4, amino acids 386-548 of SEQ ID NO: 4, amino acids 381-548 of SEQ ID NO: 4, amino acids 108-741 of SEQ ID NO: 4, amino acids 600-609 of SEQ ID NO: 6, amino acids 596-614 of SEQ ID NO: 6, amino acids 591-620 of SEQ ID NO: 6, amino acids 585-624 of SEQ ID NO: 6, or amino acids 108-802 of SEQ ID NO: 6. In some embodiments a patient is treated with an antigen binding agent that specifically binds to a SCNN1A/TNFRSF1A fusion protein consisting of amino acids 539-548 of SEQ ID NO: 4, amino acids 535-553 of SEQ ID NO: 4, amino acids 530-559 of SEQ ID NO: 4, amino acids 524-563 of SEQ ID NO: 4, amino acids 391-548 of SEQ ID NO: 4, amino acids 386-548 of SEQ ID NO: 4, amino acids 381-548 of SEQ ID NO: 4, amino acids 108-741 of SEQ ID NO: 4, amino acids 600-609 of SEQ ID NO: 6, amino acids 596-614 of SEQ ID NO: 6, amino acids 591-620 of SEQ ID NO: 6, amino acids 585-624 of SEQ ID NO: 6, or amino acids 108-802 of SEQ ID NO: 6. In some embodiments a patient is treated with an antigen binding agent that specifically binds to a SCNN1A/TNFRSF1A fusion protein that is a contiguous fragment of SEQ ID NO: 4 including at least amino acids x-553, wherein in some embodiments x is a residue selected from amino acids 1-391 and in some embodiments x is a residue selected from amino acids 108-391.

In some aspects of the invention the patient is treated with a monoclonal antibody wherein the antibody binds a SCNN1A/TNFRSF1A fusion protein with an affinity less than 1 nM and specifically binds a SCNN1A/TNFRSF1A fusion protein with at least 100-fold higher affinity than it binds either SCNN1A or TNFRSF1A.

In some aspects of the invention the patient is treated with antibodies having enhanced effector functions. In some aspects of the invention the patient is treated with antibodies conjugated to a toxin or other therapeutic agent. In some aspects of the invention the therapeutic agent is joined to the antibody by means of a cleavable or non-cleavable linker. In some aspects of the invention the therapeutic agent is an auristatin or maytansinoid.

In some aspects of the invention treatment is administered after detection of the expression of a SCNN1A/TNFRSF1A fusion protein in cells from the cancer. In some embodiments the invention provides a method of treating a patient with cancer comprising the steps of: (a) detecting expression of a SCNN1A/TNFRSF1A fusion protein in cells from the cancer, and (b) administering an antibody specifically binds to a SCNN1A/TNFRSF1A fusion protein. In some embodiments the antibody specifically binds to a SCNN1A/TNFRSF1A fusion protein selected from: (a) SEQ ID NO: 4, or a fragment thereof comprising the sequence SEQ ID NO: 1, and (b) SEQ ID NO: 6, or a fragment thereof comprising the sequence SEQ ID NO: 2.

DETAILED DESCRIPTION OF THE INVENTION

Figure 1:
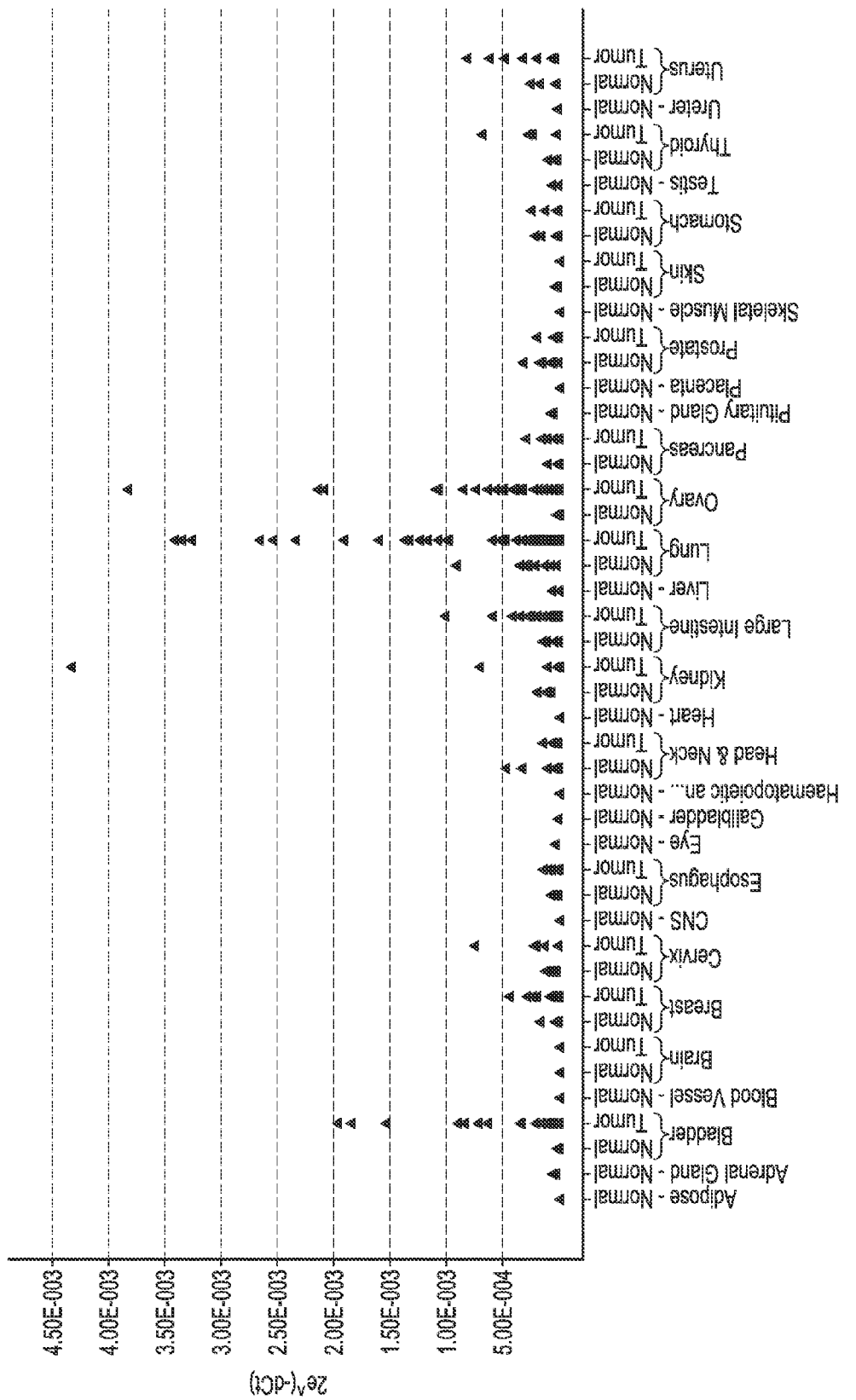
FIG. 1 shows SCNN1A 12/2 TNFRSF1A transcript expression as measured by Quantitative PCR in normal tissue samples and in tumor samples. Relative expression (2e^(-dCt)) for each tissue sample (▲) has been normalized to the expression of a housekeeping gene (beta-actin) run on the same plate.

The present invention identifies novel fusion transcripts expressed by ovarian cancer cells and other tumor type cancer cells and provides antigen binding agents, including antibodies, antibody fragments, and antibody derivatives that specifically bind to the corresponding fusion junction peptides and fusion proteins. The antigen binding agents are useful for detecting, characterizing, and treating ovarian tumors and other cancers.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al, Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

DEFINITIONS

The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The term "antigen binding agent" refers to a natural or non-natural molecule, preferably a proteinaceous molecule, that specifically binds to a target. The term "specific binding" or "specifically binds" refers to the ability of an antigen binding agent to bind to a target with greater affinity (strength of binding) than it binds to a non-target. In certain embodiments, specific binding refers to binding to a target with an affinity that is at least 10, 50, 100, 250, 500, or 1000 fold greater than the affinity for a non-target. In certain embodiments, affinity is determined by an affinity ELISA assay, by a BIAcore assay, by a kinetic method, or by an equilibrium/solution method. Affinity can be expressed in terms of the dissociation constant Kd.

Examples of antigen binding agents includes, but are not limited to proteins, peptides, nucleic acids, carbohydrates, lipids, and small molecule compounds. In some preferred embodiments of the invention the antigen binding agent is an antigen binding protein; in some preferred embodiments of the invention the antigen binding agent is an antibody.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, Proteins: Structure, Function, and Bioinformatics, Volume 53, Issue 1:121-129; Roque et al, 2004, Biotechnol. Prog. 20:639-654. In addition, peptide antibody mimetics ("PAMs") can be used, as well as scaffolds based on antibody mimetics utilizing fibronection components as a scaffold.

Antigen binding proteins further include peptibodies. The term "peptibody" refers to a molecule comprising an antibody Fc domain attached to at least one peptide. The production of peptibodies is generally described in PCT publication WO 00/24782, published May 4, 2000. Peptibodies according to the invention include those in which the peptide antigen-binding site portion(s) bind to the 12/2 or 13/2 fusion proteins, peptibodies in which one peptide recognizes SCNN1A and another peptide recognizes TNFRSF1A, and peptibodies in which one peptide recognizes the fusion protein (e.g., SCNN1A 12/2 TNFRSF1A or SCNN1A 13/2 TNFRSF1A) and another peptide recognizes TNFRSF1A or SCNN1A.

Antigen binding proteins further include nonimmunoglobulin avidity multimers or "avimers," which are multidomain proteins derived from the A-domains as found in various cell surface receptors. Avimers can be generated by the sequential selection of individual binding domains, each of which recognize a different epitope, and can therefore bind multiple sites on a target or even multiple targets See, e.g., Silverman, J. et al. Nat. Biotechnol. 23, 1556-1561 (2005).

An "epitope" is that portion of the antigen that an antigen binding agent recognizes.

An "antigen binding site" is the portion of an antigen binding agent that contains amino acid residues or other moieties that interact with an antigen and contribute to the antigen binding protein's specificity and affinity for the antigen. For an antibody that specifically binds to its antigen, this will include at least part of at least one of its CDR domains.

An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody may have two different binding sites.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2$^{nd}$ ed. Raven Press, N.Y. (1989)). The variable regions of each light/heavy chain pair form the antibody binding site such that an intact immunoglobulin has two binding sites.

Naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, 5$^{th}$ Ed., US Dept. of Health and Human Services, PHS, NIH, NIH Publication no. 91-3242, 1991. Intact antibodies include polyclonal, monoclonal, chimeric, humanized or fully human having full length heavy and light chains.

PROTEINS, NUCLEIC ACIDS, AND RECOMBINANT METHODS

The terms "peptide," "polypeptide," and "protein" each refer to a molecule comprising two or more amino acid residues joined to each other by peptide bonds. These terms encompass, e.g., native and artificial proteins, protein fragments and polypeptide analogs such as muteins, variants, and fusion proteins of a protein sequence as well as post-translationally, or otherwise covalently or non-covalently, modified proteins.

The terms "polynucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof, of the invention. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A "host cell" is a cell that can be used to express a nucleic acid, e.g., a nucleic acid of the invention. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, Cell 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, Cytotechnology 28:31) or CHO strain DX-B11, which is deficient in DHFR (see Urlaub et al., 1980, Proc. Natl. Acad. Sci. USA 77:4216-

20), HeLa cells, BHK (ATCC CRL 10) cell lines, the CV1/ EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Antigen binding proteins may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example E. coli or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CVI/EBNA cell line derived from the African green monkey kidney cell line CVI (ATCC CCL 70) as described by McMahan et al., 1991, EMBO J. 10: 2821. Appropriate cloning and expression vectors for use with bacterial, fungal, yeast, and mammalian cellular hosts are described by Pouwels et al. (*Cloning Vectors: A Laboratory Manual*, Elsevier, N.Y., 1985).

The transformed cells can be cultured under conditions that promote expression of the polypeptide, and the polypeptide recovered by conventional protein purification procedures. One such purification procedure includes the use of affinity chromatography. Polypeptides contemplated for use herein include substantially homogeneous recombinant mammalian antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest, and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

ANTIBODIES AND ANTIBODY FRAGMENTS

The term "antibody" is used in the broadest sense and includes, for example, an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include Fab, Fab', F(ab')$_2$, Fd, Fv, and domain antibodies (dAbs), and complementarity determining region (CDR) fragments, single-chain antibodies (scFv), diabodies, triabodies, tetrabodies, and polypeptides that contain at least a portion of an immunoglobulin that is sufficient to confer specific antigen binding to the polypeptide. Antibody includes a human antibody, a humanized antibody, chimeric antibody, a monoclonal antibody, a polyclonal antibody, a recombinant antibody, an antigen-binding antibody fragment, a single chain antibody, a maxibody (scFv fused by a linker or direct attachment to an Fc or an Fc fragment), a diabody, a triabody, a tetrabody, a Fab fragment, an F(fa')x fragment, a domain antibody, an IgD antibody, an IgE antibody, and IgM antibody, and IgG1 antibody, and IgG2 antibody, and IgG3 antibody, and IgG4 antibody, and IgG4 antibody having at least one mutation in the hinge region that alleviates a tendency to for intra H-chain disulfide bonds.

The term "polyclonal antibody" refers to a heterogeneous mixture of antibodies that bind to different epitopes of the same antigen.

The term "monoclonal antibodies" refers to a collection of antibodies encoded by the same nucleic acid molecule. In certain embodiments, monoclonal antibodies are produced by a single hybridoma or other cell line, or by a transgenic mammal. Monoclonal antibodies typically recognize the same epitope. The term "monoclonal" is not limited to any particular method for making an antibody.

A "Fab fragment" is a monovalent fragment having the $V_L$, $V_H$, $C_L$ and $C_H1$ domains; a F(ab')$_2$ fragment is a bivalent fragment having two Fab fragments linked by a disulfide bridge at the hinge region; a Fd fragment has the $V_H$ and $C_H1$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain.

A "single-chain antibody" (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, Science 242:423-26 and Huston et al, 1988, Proc. Natl. Acad. Sci. USA 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48, and Poljak et al., 1994, Structure 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. in Sequences of Proteins of Immunological Interest, 5$^{th}$ Ed., US Dept. of Health and Human Services, PHS, NIH, NIH Publication no. 91-3242, 1991. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

The term "human antibody" includes all antibodies that have one or more variable and constant regions derived from human immunoglobulin sequences. In one embodiment, all of the variable and constant domains are derived from human immunoglobulin sequences (a fully human antibody). Human antibodies may be prepared in a variety of ways, including immunization of a mouse that is genetically modified to express human antibodies. One can engineer mouse strains deficient in mouse antibody production with large fragments of the human Ig loci in anticipation that such mice would produce human antibodies in the absence of mouse antibodies. Large human Ig fragments may preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains may yield high affinity fully human antibodies against any antigen of interest, including human antigens. Using the hybridoma technology, antigen-specific human MAbs with the desired specificity may be produced and selected. Certain exemplary methods are described in WO 98/24893, U.S. Pat. No. 5,545,807, EP 546073B1, and EP 546073A1. Human antibodies can also be prepared by panning human antibody libraries expressed on phage, phagemids, ribosomes, or other particles.

A "humanized antibody" has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of methods for making humanized antibodies may be found in U.S. Pat. Nos. 6,054, 297, 5,886,152 and 5,877,293.

The term "chimeric antibody" refers to an antibody that contains one or more regions from one antibody and one or more regions from one or more other antibodies. A "CDR grafted antibody" is an antibody comprising one or more CDRs derived from an antibody of a particular species or isotype and the framework of another antibody of the same or different species or isotype.

Fragments or analogs of antibodies can be readily prepared by those of ordinary skill in the art following the teachings of this specification and using techniques well-known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, e.g., Bowie et al, 1991, Science 253:164.

The term "multispecific antibody" refers to an antibody wherein two or more variable regions bind to different epitopes. The epitopes may be on the same or different targets. In certain embodiments, a multispecific antibody is a "bispecific antibody," which recognizes two different epitopes on the same or different antigens.

Numerous methods of preparing bispecific antibodies are known in the art, and discussed in, e.g., U.S. patent application Ser. No. 09/839,632, filed Apr. 20, 2001 (incorporated by reference herein). Such methods include the use of hybrid-hybridomas as described by Milstein et al., 1983, Nature 305:537, and others (U.S. Pat. No. 4,474,893, U.S. Pat. No. 6,106,833), and chemical coupling of antibody fragments (Brennan et al., 1985, Science 229:81; Glennie et al., 1987, J. Immunol. 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, J. Immnol. 148:1547) or other lock and key interactive domain structures as described in U.S. Pat. No. 5,582,996. Additional useful techniques include those described in Kortt et al., 1997, supra; U.S. Pat. No. 5,959,083; and U.S. Pat. No. 5,807,706.

In the case of an antibody that binds a protein target, an "epitope" is the antigenic site on the protein that is recognized by the antibody, i.e., the minimum molecular structure within the protein target to which the antibody binds. Epitopes on proteins may be continuous (comprising a segment of continuous amino acids from the primary amino acid sequence) or non-continuous (comprising amino acids that are not continuous in the primary protein sequence but which are in close proximity in the three-dimensional folded protein).

Antibodies according to the invention will typically have a Kd in the range of $10^{-7}$ to $10^{-13}$ M; in some preferred embodiments the antibodies have a Kd of less than $10^{-9}$ M. The antibodies of the invention specifically bind to the disclosed fusion proteins with higher affinity than they bind to other targets, including to the individual fusion partners SCNN1A and TNFRSF1A. In some preferred embodiments the antibodies bind the SCNN1A 12/2 TNFRSF1A fusion protein with at least 10-fold higher affinity than they bind either of the SCNN1A or TNFRSF1A fusion partners; in some preferred embodiments the antibodies bind the SCNN1A 12/2

TNFRSF1A fusion protein with at least 100-fold higher affinity than they bind either of the SCNN1A or TNFRSF1A fusion partners. In some preferred embodiments the antibodies bind the SCNN1A 13/2 TNFRSF1A fusion protein with at least 10-fold higher affinity than they bind either of the SCNN1A or TNFRSF1A fusion partners; in some preferred embodiments the antibodies bind the SCNN1A 13/2 TNFRSF1A fusion protein with at least 100-fold higher affinity than they bind either of the SCNN1A or TNFRSF1A fusion partners.

In some embodiments of the invention a bispecific binding agent, e.g., a bispecific antibody, recognizes the fusion proteins, with one antigen-binding site recognizing SCNN1A and another antigen-binding site recognizing TNFRSF1A. In some embodiments, one antigen-binding site recognizes the fusion protein (e.g., SCNN1A 12/2 TNFRSF1A or SCNN1A 13/2 TNFRSF1A) and another antigen-binding site recognizes TNFRSF1A. In some embodiments, one antigen-binding site recognizes the fusion protein (e.g., SCNN1A 12/2 TNFRSF1A or SCNN1A 13/2 TNFRSF1A) and another antigen-binding site recognizes SCNN1A. In some embodiments one antigen-binding site recognizes the fusion protein and another antigen-binding site recognizes another antigen such as, e.g., an antigen expressed on a T-cell in order to leverage the cytotoxicity of T cells. In some embodiments the bispecific antibodies have a lower affinity, e.g., a Kd of greater than 100 nM for each arm, in order to take advantage of the avidity enhancement that can result from bispecific binding.

METHODS OF USING THE INVENTION TO IDENTIFY AND CHARACTERIZE TUMORS

As illustrated in Example 3, the fusion proteins described herein are differentially expressed in certain tumors, including ovarian, lung, thyroid, and bladder tumors, as compared to normal tissues. Detecting expression and/or expression levels of the fusion proteins in tissue samples can therefore be used to identify a tumor, characterize a tumor, or to monitor the effects of treatment on tumors that express the identified fusion proteins. In some embodiments expression is detected at the RNA level, using methods described herein and known in the art such as Quantitative PCR, hybridization, in situ hybridization, nanostring technology (such as that described in U.S. Pat. No. 7,473,767), and nucleic acid sequencing. In some embodiments expression is detected at the protein level, using methods described herein and known in the art such as immunoprecipitation, immunohistochemistry (IHC), Western blot analysis, flow cytometry, ELISA, immunoassays with antibody detection, and mass spectrometry.

METHODS OF USING THE INVENTION TO INHIBIT PROLIFERATION AND TREAT CANCER

The antibodies or other antigen binding agents of the invention may be used to inhibit proliferation of cells that express the identified fusion proteins, including for the treatment of ovarian, lung, bladder, thyroid, and other cancers.

In certain embodiments, the antibodies or other antigen binding agents are administered alone. In certain embodiments, the antibodies or other antigen binding agents are administered prior to the administration of at least one other therapeutic agent. In certain embodiments, the antibodies or other antigen binding agents are administered concurrent with the administration of at least one other therapeutic agent. In certain embodiments, the antibodies or other antigen binding agents are administered subsequent to the administration of at least one other therapeutic agent. Exemplary therapeutic agents include, but are not limited to, radiation therapy and chemotherapy.

The antibodies or other antigen binding agents are administered in a pharmaceutical composition including materials for modifying, maintaining or preserving, for example, the pH, osmolarity, viscosity, clarity, color, isotonicity, odor, sterility, stability, rate of dissolution or release, adsorption or penetration of the composition. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol. The optimal pharmaceutical composition will be determined by one skilled in the art depending upon, for example, the intended route of administration, delivery format and desired dosage. Delivery vehicles, diluents, excipients, and pharmaceutical adjuvants are known in the art and described in, e.g., *Remington's Pharmaceutical Sciences*, 18$^{th}$ Edition, A. R. Gennaro, ed., Mack Publishing Company (1990).

The route of antibody administration is in accord with known methods, e.g., injection or infusion by intravenous, intraperitoneal, intracerebral, intramuscular, intraocular, intraarterial, intrathecal, inhalation or intralesional routes, or by sustained release systems as noted below. Antibodies are preferably administered continuously by infusion or by bolus injection. An effective amount of antibody to be employed therapeutically will depend, for example, upon the therapeutic objectives, the route of administration, and the condition of the patient. The dosage of the antibody formulation for a given patient will be determined by the attending physician taking into consideration various factors known to modify the action of drugs including severity and type of disease, body weight, sex, diet, time and route of administration, other medications and other relevant clinical factors.

In some embodiments of the invention the antibodies or other antigen binding agents are able to directly modulate the function of the fusion proteins and therefore selectively kill tumor cells expressing those fusion proteins.

In some embodiments of the invention, the cell killing ability of antibodies is improved through conjugation to a cytotoxic agent or by enhancing an antibody effector function. These embodiments are particularly well-suited to killing cancer cells that express the fusion proteins of the invention. Antibodies with improved cell-killing ability, such as antibodies conjugated to a toxin or antibodies with enhanced effector function, can be used to kill tumor cells expressing the fusion proteins whether or not those fusion proteins are functional and whether or not the antibodies modulate that function. This is an important therapeutic advantage in the treatment of tumors.

The invention therefore includes compositions and use of "antibody-drug conjugates," or "ADCs" (which are also referred to immunoconjugates) comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate). The use of antibody-drug conjugates for the local delivery of cytotoxic or cytostatic agents, i.e. drugs to kill or inhibit tumor cells in the treatment of cancer (Lambert, J. (2005) Curr. Opinion in Pharmacology 5:543-549; Wu et al (2005) Nature Biotechnology 23(9): 1 137-L 146; Payne, G. (2003) Cancer Cell 3:207-212; Syrigos and Epenetos (1999) Anticancer Research 19:605-614; Nicutescu-Duvaz and Springer (1997) Adv. Drug Del. Rev. 26: 151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al (ed.s), pp. 475-506). Efforts to improve the therapeutic index, i.e. maximal efficacy and minimal toxicity of ADC have focused on the selectivity of polyclonal (Rowland et al (1986) Cancer Immunol. Immunother., 21: 183-87) and monoclonal antibodies (mAbs) as well as drug-linking and drug-releasing properties (Lambert, J. (2005) Curr. Opinion in Pharmacology 5:543-549). Drug moieties used in antibody drug conjugates include bacterial protein toxins such as diphtheria toxin, plant protein toxins such as ricin and saporin, small molecules such as auristatins, geldanamycin (Mandler et al (2000) J. of the Nat. Cancer Inst. 92(19): 1573-1581; Mandler et al (2000) Bioorganic & Med. Chem. Letters 10: 1025-1028; Mandler et al (2002) Bioconjugate Chem. 13:786-791), maytansinoids (EP 1391213; Liu et al (1996) Proc. Natl. Acad. Sci. USA 93:8618-8623), calicheamicin (Lode et al (1998) Cancer Res. 58:2928; Hinman et al (1993) Cancer Res. 53:3336-3342), daunomycin, doxorubicin, methotrexate, and vindesine.

In some embodiments of the invention the antibodies have an enhanced effector function. Antibody "effector function" refers to those biological activities attributable to the Fc region of an antibody, including complement-dependent cytotoxicity (CDC) and antibody-dependent cell-mediated cytotoxicity (ADCC). ADCC is a cell-mediated reaction in which nonspecific cytotoxic cells that express Fc receptors recognize bound antibody on a target cell and subsequently cause lysis of the target cell. In some embodiments, the ADCC activity of the antibodies has been enhanced through methods known in the art such as modification of the Fc sequence or modification of the carbohydrate structure, e.g., reducing fucose in the Fc-linked oligosaccharide structure of the antibodies to create "afucosylated antibodies."

EXAMPLES

Example 1

Sequencing Ovarian Cancer Transcriptomes

RNA was extracted from eight samples: three ovarian serous adenocarcinoma stage 3 grade 3 tumors; three unmatched normal ovary; and two mixtures of multiple essential normal tissues, including colon, right atrium, liver, ventricle, esophagus, kidney, small intestine, lung, adrenal cortex, pituitary, pancreas, and stomach. The RNA was reverse transcribed and the resulting DNA sequenced to identify potential tumor-specific antigens. Using next generation sequencing, which can generate 100,000-fold or more sequence information as compared to capillary sequencing methods, yielded information about the identity and abundance of sequences within the transcriptomes. A comparison of sequences from the ovarian cancer samples as compared to the normal tissues identified differentially expressed genes, novel exons and splice junctions, and transcript fusions. Of approx. 7000 genes found to be overexpressed, 46 genes were upregulated at least 20-fold in ovarian tumors as compared to normal tissues and twelve were predicted to encode tumor-specific cell surface proteins. Of 350 transcript fusion candidates in which individual or paired sequence reads were mapped to two different genes, eight were tumor-specific and at least three were predicted to encode cell surface proteins. The transcriptomes of eight additional ovarian tumors as well as additional normal ovary, fallopian tube, and other normal tissues were also sequenced and two ovarian cancer-specific fusion proteins were further characterized as described in Examples 2 and 3.

Example 2

Identification and Sequencing of Ovarian Cancer Fusion Protiens

Two fusion transcripts between adjacent genes SCNN1A (NCBI Reference Sequence: NM_001038.5, Homo sapiens sodium channel, non-voltage-gated 1 alpha subunit) and TNFRSF1A (NCBI Reference Sequence: NM_001065.2, Homo sapiens tumor necrosis factor receptor superfamily, member 1A) were specifically found in ovarian tumors vs. normal tissues and were predicted to encode cell surface proteins. Using cDNA prepared from RNA from ovarian tumors and ovarian cancer cell lines, the fusion junctions were confirmed. Additional characterization of the fusion transcripts by RACE-PCR (rapid amplification of cDNA ends polymerase chain reaction) revealed multiple potential full length fusion cDNA sequences, all of which contained the fusion junctions as described below.

The SCNN1A 12/2 TNFRSF1A fusion ("the 12/2 fusion") is believed to result from tumor-specific splicing between exon 12 of SCNN1A and exon 2 of TNFRSF1A, and includes the fusion junction peptide sequence TNSESPSVT-VL-LELLVGIY (SEQ ID NO: 1; the "-" shows the point of fusion). A predicted full length cDNA sequence corresponding to a fused SCNN1A 12/2 TNFRSF1A transcript is shown as SEQ ID NO: 3. The deduced amino acid sequence of the fusion protein is shown as SEQ ID NO: 4. The fusion junction peptide is shown as residues 535-553 of SEQ ID NO: 4.

The SCNN1A 13/2 TNFRSF1A fusion ("the 13/2 fusion") is believed to result from tumor-specific splicing between exon 13 of SCNN1A and exon 2 of TNFRSF1A, and includes the fusion junction peptide sequence GRGGRGAQE-VL-LELLVGIY (SEQ ID NO: 2; the "-" shows the point of fusion). A predicted full length cDNA sequence corresponding to a fused SCNN1A 13/2 TNFRSF1A transcript is shown as SEQ ID NO: 5. The deduced amino acid sequence of the fusion protein is shown as SEQ ID NO: 6. The fusion junction peptide is shown as residues 596-614 of SEQ ID NO: 6.

SCNN1A-TNFRSF1A fusions were observed in all eleven ovarian tumors sequenced.

SCNN1A occurs in different isoforms, including NM 001038.5/NP 001029.1, NM_001159576.1/NP_ 001153048.1, and NM_001159575.1/N_001153047.1, and tumor-specific splicing can involve any of these isoforms. In some fusion proteins, therefore, the deduced amino acid sequence of the fusion protein has an additional 59 amino acids (MGMARGSLTR VPGVMGEGTQ GPELSLDPDP CSPQSTPGLM KGNKLEEQDP RPLQPIPGL, SEQ ID NO: 13) at the N-terminus. In other fusion proteins, the deduced amino acid sequence of the fusion protein has an additional 23 amino acids, (MSSIKGNKLE EQDPRPLQPI PGL, SEQ ID NO: 14) at the N-terminus.

Example 3

SCNN1A-TNFRSF1a Fusion Protein Expression

Quantitative RT-PCR methods were developed to specifically detect each fusion. For the 12/2 fusion, the junction site was amplified by primers 5'-CATCTTCTTCAAG GAGCT-GAACTACA-3' (SEQ ID NO: 7) and 5'-GACCAGTC-CAATAACCCCTGAG-3' (SEQ ID NO: 8), and detected with a fluorescently-labeled TaqMan® (Real-Time PCR, Applied Biosystems) hydrolysis probe 5'-6FAM-CTGT-CACGGTGCTCCT-MGB-3' (SEQ ID NO: 9, where 6FAM and MGB are a 6-carboxyfluorescein fluorophore and a dihydrocyclopyrroloindole tripeptide minor groove binder quencher respectively) covering the junction site.

For the 13/2 fusion, the junction site was amplified by primers 5'-CCGAAGC CGATACTGGTCTC-3' (SEQ ID NO: 10) and 5'-GACCAGTCCAATAACCCCTGAG-3' (SEQ ID NO: 11), and detected with a fluorescently-labeled TaqMan® (Real-Time PCR, Applied Biosystems) hydrolysis probe 5'-6FAM-CTCAGGAGGTGCTCCT-MGB-3' (SEQ ID NO: 12, where 6FAM and MGB are a 6-carboxyfluorescein fluorophore and a dihydrocyclopyrroloindole tripeptide minor groove binder quencher respectively) covering the junction site.

Figure 2:
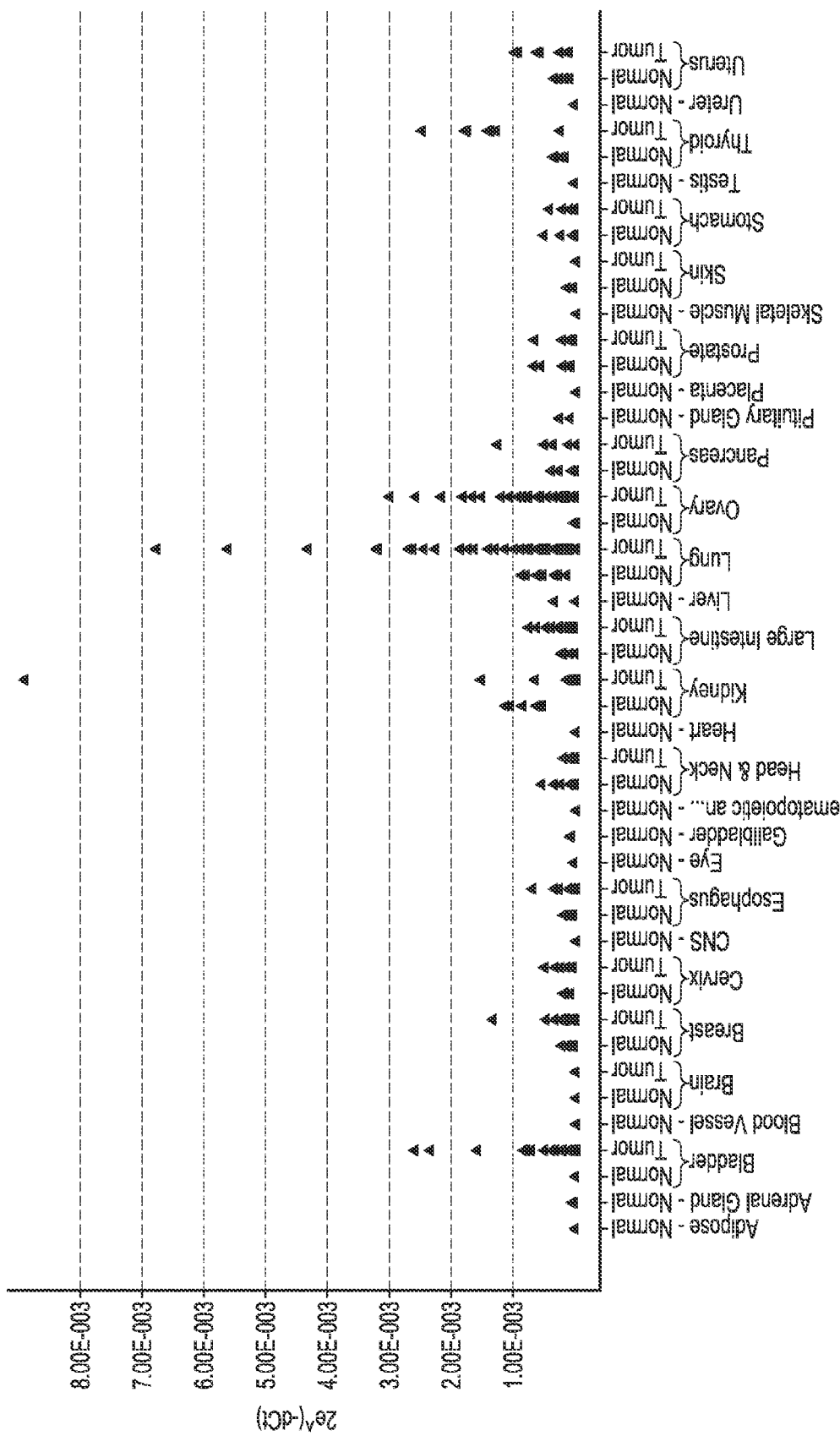
FIG. 2 shows SCNN1A 13/2 TNFRSF1A transcript expression as measured by Quantitative PCR in normal tissue samples and in tumor samples. Relative expression (2e^(-dCt)) for each tissue sample (▲) has been normalized to the expression of a housekeeping gene (beta-actin) run on the same plate.

As shown in FIGS. 1 and 2, quantitative PCR analysis confirmed that SCNN1A-TNFRSF1A fusion proteins are preferentially expressed in ovarian cancer tissue as compared to normal tissues. Quantitative PCR also detected differential expression of the fusions in lung, thyroid, and bladder tumors as compared to normal tissues. Albeit low, there was detectable expression of the fusions in some normal tissues, such as lung and kidney.

Immunoprecipitation and Western Blot analysis showed that cancer cell lines which had been identified as expressing fusion messages also express fusion proteins. A commercially available anti-TNFR antibody was used to immunoprecipitate protein from cell lysates which were then analyzed by Western Blot using a commercially available anti-SCNN1A antibody. This revealed the presence of a band near the estimated MW of the fusion proteins in cell lines positive for fusion message that was absent in those cell lines negative for fusion message.

Additionally, mass spectrometric identification of peptides from both fusion partners (SCNN1A and TNFRSF1A) was obtained by analyzing the protein in the gel excised at the fusion protein band location (neither wildtype protein migrates at this location). The ratio of SI(N) (Normalized Spectral Index) values calculated for the fusion partners were consistent with a 1:1 stoichiometry between SCNN1A and TNFRSF1A, further substantiating expression of the fusion proteins.

Example 4

Antibodies to Fusion Peptides and Fusion Proteins

The fusion junction peptides of SEQ ID NOs: 1 and 2 were separately synthesized and used as antigens to make polyclonal or monoclonal antibodies using standard techniques known in the art.

Longer fragments containing the junction peptides were also used as antigens to generate antibodies, e.g., for the 12/2 fusion ELNYKTNSESPSVTVLLELLVGIYPSGVIG (residues 530-559 of SEQ ID NO: 4) and for the 13/2 fusion RYWSPGRGGRGAQEVLL ELLVGIYPSGVIG (residues 591-620 of SEQ ID NO: 6).

Fragments containing the junction peptides and predicted to include extracellular domains are also used as antigens to generate antibodies, e.g., for the 12/2 fusion residues 108-741 of SEQ ID NO: 4 and for the 13/2 fusion residues 108-802 of SEQ ID NO: 6.

Additional antibodies are similarly made to the fusion proteins shown in SEQ ID NOs: 4 and 6 and to the fusion proteins and fragments thereof that are expressed on a recombinant host cell.

The antibodies generated against the fusion junction peptides, fusion proteins, and expressed fusion proteins are used to confirm protein expression and study protein localization in ovarian and other tumors, to detect and characterize ovarian and other tumors, and to treat ovarian cancer and other cancers including lung cancer, thyroid cancer, and bladder cancer.

Human antibodies that specifically bind to the SCNN1A-TNFRSF1A fusion proteins are particularly useful for treating cancers including lung cancer, thyroid cancer, and bladder cancer. Human antibodies that specifically bind to the SCNN1A-TNFRSF1A fusion proteins and are conjugated to a cytotoxic agent and/or modified to have an enhanced effector function are particularly useful for treating cancers including lung cancer, thyroid cancer, and bladder cancer.

What is claimed is:

1. An isolated antibody that specifically binds to a SCNN1A/TNFRSF1A fusion protein.

2. The antibody of claim 1, wherein the antibody specifically binds to a SCNN1A/TNFRSF1A fusion protein selected from:
    (a) SEQ ID NO: 6, and a fragment thereof comprising the sequence SEQ ID NO: 2, and
    (b) SEQ ID NO: 4, and a fragment thereof comprising the sequence SEQ ID NO: 1.

3. The antibody of claim 2, wherein the antibody is a monoclonal antibody.

4. The monoclonal antibody of claim 3, wherein the antibody specifically binds the SCNN1A/TNFRSF1A fusion protein with at least 100-fold higher affinity than it binds either SCNN1A or TNFRSF1A.

5. The monoclonal antibody of claim 4, wherein the antibody is conjugated to a cytotoxic agent.

6. The monoclonal antibody of claim 5, wherein the cytotoxic agent is an auristatin or maytansinoid.

7. The monoclonal antibody of claim 4, wherein the antibody has an enhanced effector function.

8. The antibody of claim 1, wherein the antibody is a bispecific antibody in which one antigen-binding site binds an epitope on SCNN1A and one antigen-binding site binds an epitope on TNFRSF1A.

9. The bispecific antibody of claim 8, wherein the antibody specifically binds to a SCNN1A/TNFRSF1A fusion protein selected from:
    (a) SEQ ID NO: 6, and a fragment thereof comprising the sequence SEQ ID NO: 2, and
    (b) SEQ ID NO: 4, and a fragment thereof comprising the sequence SEQ ID NO: 1.

10. An isolated antibody that binds to a SCNN1A/TNFRSF1A fusion protein consisting of a sequence selected from SEQ ID NO:6 and SEQ ID NO:4 with at least 10-fold higher affinity than it binds to the individual fusion partners SCNN1A and TNFRSF1A.

11. The antibody of claim 10 that binds to the fusion protein with at least 100-fold higher affinity.

12. The antibody of claim 10 wherein the fusion protein is SEQ ID NO:6.

13. The antibody of claim 10 wherein the fusion protein is SEQ ID NO:4.

14. The antibody of claim 1 that specifically binds to SEQ ID NO: 2 or SEQ ID NO:1.

15. The antibody of claim 1 that specifically binds to residues 530-559 of SEQ ID NO: 4 or residues 591-620 of SEQ ID NO: 6.

16. The antibody of claim 1 that specifically binds to residues 108-741 of SEQ ID NO: 4 or residues 108-802 of SEQ ID NO: 6.

17. A method of identifying or characterizing a tumor comprising detecting expression in cells from the tumor of a fusion protein selected from:
    (a) SEQ ID NO: 6, and a fragment thereof comprising the sequence SEQ ID NO: 2, and
    (b) SEQ ID NO: 4, and a fragment thereof comprising the sequence SEQ ID NO: 1, wherein the fusion protein is detected using the antibody of claim 1.

* * * * *

SEQUENCE LISTING

```
<160> NUMBER OF SEQ ID NOS: 14

<210> SEQ ID NO 1
<211> LENGTH: 19
<212> TYPE: PRT
<213> ORGANISM: Homo sapiens

<400> SEQUENCE: 1

Thr Asn Ser Glu Ser Pro Ser Val Thr Val Leu Leu Glu Leu Leu Val
1               5                   10                  15

Gly Ile Tyr

<210> SEQ ID NO 2
<211> LENGTH: 19
```

```
<212> TYPE: PRT
<213> ORGANISM: Homo sapiens

<400> SEQUENCE: 2

Gly Arg Gly Gly Arg Gly Ala Gln Glu Val Leu Leu Glu Leu Leu Val
1               5                   10                  15

Gly Ile Tyr

<210> SEQ ID NO 3
<211> LENGTH: 3834
<212> TYPE: DNA
<213> ORGANISM: Homo sapiens
<220> FEATURE:
<221> NAME/KEY: CDS
<222> LOCATION: (290)..(3247)

<400> SEQUENCE: 3
cttgcctgtc tgcgtctaaa gcccctgccc agagtccgcc ttctcaggtc cagtactccc     60
agttcacctg ccctcgggag ccctccttcc ttcggaaaac tcccggctct gactcctcct    120
cagcccctcc ccccgccctg ctcaccttta attgagatgc taatgagatt cctgtcgctt    180
ccatccctgg ccggccagcg ggcgggctcc ccagccaggc cgctgcacct gtcaggggaa    240
caagctggag gagcaggacc ctagacctct gcagcccata ccaggtctc atg gag ggg    298
                                                      Met Glu Gly
                                                        1 aac aag ctg gag gag cag gac tct agc cct cca cag tcc act cca ggg      346
Asn Lys Leu Glu Glu Gln Asp Ser Ser Pro Pro Gln Ser Thr Pro Gly
        5                   10                  15 ctc atg aag ggg aac aag cgt gag gag cag ggg ctg ggc ccc gaa cct      394
Leu Met Lys Gly Asn Lys Arg Glu Glu Gln Gly Leu Gly Pro Glu Pro
20                  25                  30                  35 gcg gcg ccc cag cag ccc acg gcg gag gag gag gcc ctg atc gag ttc      442
Ala Ala Pro Gln Gln Pro Thr Ala Glu Glu Glu Ala Leu Ile Glu Phe
                40                  45                  50 cac cgc tcc tac cga gag ctc ttc gag ttc ttc tgc aac aac acc acc      490
His Arg Ser Tyr Arg Glu Leu Phe Glu Phe Phe Cys Asn Asn Thr Thr
            55                  60                  65 atc cac ggc gcc atc cgc ctg gtg tgc tcc cag cac aac cgc atg aag      538
Ile His Gly Ala Ile Arg Leu Val Cys Ser Gln His Asn Arg Met Lys
        70                  75                  80 acg gcc ttc tgg gca gtg ctg tgg ctc tgc acc ttt ggc atg atg tac      586
Thr Ala Phe Trp Ala Val Leu Trp Leu Cys Thr Phe Gly Met Met Tyr
85                  90                  95 tgg caa ttc ggc ctg ctt ttc gga gag tac ttc agc tac ccc gtc agc      634
Trp Gln Phe Gly Leu Leu Phe Gly Glu Tyr Phe Ser Tyr Pro Val Ser
100                 105                 110                 115 ctc aac atc aac ctc aac tcg gac aag ctc gtc ttc ccc gca gtg acc      682
Leu Asn Ile Asn Leu Asn Ser Asp Lys Leu Val Phe Pro Ala Val Thr
            120                 125                 130 atc tgc acc ctc aat ccc tac agg tac ccg gaa att aaa gag gag ctg      730
Ile Cys Thr Leu Asn Pro Tyr Arg Tyr Pro Glu Ile Lys Glu Glu Leu
        135                 140                 145 gag gag ctg gac cgc atc aca gag cag acg ctc ttt gac ctg tac aaa      778
Glu Glu Leu Asp Arg Ile Thr Glu Gln Thr Leu Phe Asp Leu Tyr Lys
    150                 155                 160 tac agc tcc ttc acc act ctc gtg gcc ggc tcc cgc agc cgt cgc gac      826
Tyr Ser Ser Phe Thr Thr Leu Val Ala Gly Ser Arg Ser Arg Arg Asp
165                 170                 175 ctg cgg ggg act ctg ccg cac ccc ttg cag cgc ctg agg gtc ccg ccc      874
Leu Arg Gly Thr Leu Pro His Pro Leu Gln Arg Leu Arg Val Pro Pro
180                 185                 190                 195
```

```
ccg cct cac ggg gcc cgt cga gcc cgt agc gtg gcc tcc agc ttg cgg       922
Pro Pro His Gly Ala Arg Arg Ala Arg Ser Val Ala Ser Ser Leu Arg
            200                 205                 210 gac aac aac ccc cag gtg gac tgg aag gac tgg aag atc ggc ttc cag       970
Asp Asn Asn Pro Gln Val Asp Trp Lys Asp Trp Lys Ile Gly Phe Gln
            215                 220                 225 ctg tgc aac cag aac aaa tcg gac tgc ttc tac cag aca tac tca tca      1018
Leu Cys Asn Gln Asn Lys Ser Asp Cys Phe Tyr Gln Thr Tyr Ser Ser
            230                 235                 240 ggg gtg gat gcg gtg agg gag tgg tac cgc ttc cac tac atc aac atc      1066
Gly Val Asp Ala Val Arg Glu Trp Tyr Arg Phe His Tyr Ile Asn Ile
        245                 250                 255 ctg tcg agg ctg cca gag act ctg cca tcc ctg gag gag gac acg ctg      1114
Leu Ser Arg Leu Pro Glu Thr Leu Pro Ser Leu Glu Glu Asp Thr Leu
260                 265                 270                 275 ggc aac ttc atc ttc gcc tgc cgc ttc aac cag gtc tcc tgc aac cag      1162
Gly Asn Phe Ile Phe Ala Cys Arg Phe Asn Gln Val Ser Cys Asn Gln
                280                 285                 290 gcg aat tac tct cac ttc cac cac ccg atg tat gga aac tgc tat act      1210
Ala Asn Tyr Ser His Phe His His Pro Met Tyr Gly Asn Cys Tyr Thr
            295                 300                 305 ttc aat gac aag aac aac tcc aac ctc tgg atg tct tcc atg cct gga      1258
Phe Asn Asp Lys Asn Asn Ser Asn Leu Trp Met Ser Ser Met Pro Gly
            310                 315                 320 atc aac aac ggt ctg tcc ctg atg ctg cgc gca gag cag aat gac ttc      1306
Ile Asn Asn Gly Leu Ser Leu Met Leu Arg Ala Glu Gln Asn Asp Phe
        325                 330                 335 att ccc ctg ctg tcc aca gtg act ggg gcc cgg gta atg gtg cac ggg      1354
Ile Pro Leu Leu Ser Thr Val Thr Gly Ala Arg Val Met Val His Gly
340                 345                 350                 355 cag gat gaa cct gcc ttt atg gat gat ggt ggc ttt aac ttg cgg cct      1402
Gln Asp Glu Pro Ala Phe Met Asp Asp Gly Gly Phe Asn Leu Arg Pro
                360                 365                 370 ggc gtg gag acc tcc atc agc atg agg aag gaa acc ctg gac aga ctt      1450
Gly Val Glu Thr Ser Ile Ser Met Arg Lys Glu Thr Leu Asp Arg Leu
            375                 380                 385 ggg ggc gat tat ggc gac tgc acc aag aat ggc agt gat gtt cct gtt      1498
Gly Gly Asp Tyr Gly Asp Cys Thr Lys Asn Gly Ser Asp Val Pro Val
        390                 395                 400 gag aac ctt tac cct tca aag tac aca cag cag gtg tgt att cac tcc      1546
Glu Asn Leu Tyr Pro Ser Lys Tyr Thr Gln Gln Val Cys Ile His Ser
        405                 410                 415 tgc ttc cag gag agc atg atc aag gag tgt ggc tgt gcc tac atc ttc      1594
Cys Phe Gln Glu Ser Met Ile Lys Glu Cys Gly Cys Ala Tyr Ile Phe
420                 425                 430                 435 tat ccg cgg ccc cag aac gtg gag tac tgt gac tac aga aag cac agt      1642
Tyr Pro Arg Pro Gln Asn Val Glu Tyr Cys Asp Tyr Arg Lys His Ser
                440                 445                 450 tcc tgg ggg tac tgc tac tat aag ctc cag gtt gac ttc tcc tca gac      1690
Ser Trp Gly Tyr Cys Tyr Tyr Lys Leu Gln Val Asp Phe Ser Ser Asp
            455                 460                 465 cac ctg ggc tgt ttc acc aag tgc cgg aag cca tgc agc gtg acc agc      1738
His Leu Gly Cys Phe Thr Lys Cys Arg Lys Pro Cys Ser Val Thr Ser
        470                 475                 480 tac cag ctc tct gct ggt tac tca cga tgg ccc tcg gtg aca tcc cag      1786
Tyr Gln Leu Ser Ala Gly Tyr Ser Arg Trp Pro Ser Val Thr Ser Gln
    485                 490                 495 gaa tgg gtc ttc cag atg cta tcg cga cag aac aat tac acc gtc aac      1834
Glu Trp Val Phe Gln Met Leu Ser Arg Gln Asn Asn Tyr Thr Val Asn
500                 505                 510                 515
```

```
aac aag aga aat gga gtg gcc aaa gtc aac atc ttc ttc aag gag ctg      1882
Asn Lys Arg Asn Gly Val Ala Lys Val Asn Ile Phe Phe Lys Glu Leu
            520                 525                 530 aac tac aaa acc aat tct gag tct ccc tct gtc acg gtg ctc ctg gag      1930
Asn Tyr Lys Thr Asn Ser Glu Ser Pro Ser Val Thr Val Leu Leu Glu
            535                 540                 545 ctg ttg gtg gga ata tac ccc tca ggg gtt att gga ctg gtc cct cac      1978
Leu Leu Val Gly Ile Tyr Pro Ser Gly Val Ile Gly Leu Val Pro His
            550                 555                 560 cta ggg gac agg gag aag aga gat agt gtg tgt ccc caa gga aaa tat      2026
Leu Gly Asp Arg Glu Lys Arg Asp Ser Val Cys Pro Gln Gly Lys Tyr
    565                 570                 575 atc cac cct caa aat aat tcg att tgc tgt acc aag tgc cac aaa gga      2074
Ile His Pro Gln Asn Asn Ser Ile Cys Cys Thr Lys Cys His Lys Gly
580                 585                 590                 595 acc tac ttg tac aat gac tgt cca ggc ccg ggg cag gat acg gac tgc      2122
Thr Tyr Leu Tyr Asn Asp Cys Pro Gly Pro Gly Gln Asp Thr Asp Cys
            600                 605                 610 agg gag tgt gag agc ggc tcc ttc acc gct tca gaa aac cac ctc aga      2170
Arg Glu Cys Glu Ser Gly Ser Phe Thr Ala Ser Glu Asn His Leu Arg
            615                 620                 625 cac tgc ctc agc tgc tcc aaa tgc cga aag gaa atg ggt cag gtg gag      2218
His Cys Leu Ser Cys Ser Lys Cys Arg Lys Glu Met Gly Gln Val Glu
            630                 635                 640 atc tct tct tgc aca gtg gac cgg gac acc gtg tgt ggc tgc agg aag      2266
Ile Ser Ser Cys Thr Val Asp Arg Asp Thr Val Cys Gly Cys Arg Lys
    645                 650                 655 aac cag tac cgg cat tat tgg agt gaa aac ctt ttc cag tgc ttc aat      2314
Asn Gln Tyr Arg His Tyr Trp Ser Glu Asn Leu Phe Gln Cys Phe Asn
660                 665                 670                 675 tgc agc ctc tgc ctc aat ggg acc gtg cac ctc tcc tgc cag gag aaa      2362
Cys Ser Leu Cys Leu Asn Gly Thr Val His Leu Ser Cys Gln Glu Lys
            680                 685                 690 cag aac acc gtg tgc acc tgc cat gca ggt ttc ttt cta aga gaa aac      2410
Gln Asn Thr Val Cys Thr Cys His Ala Gly Phe Phe Leu Arg Glu Asn
            695                 700                 705 gag tgt gtc tcc tgt agt aac tgt aag aaa agc ctg gag tgc acg aag      2458
Glu Cys Val Ser Cys Ser Asn Cys Lys Lys Ser Leu Glu Cys Thr Lys
            710                 715                 720 ttg tgc cta ccc cag att gag aat gtt aag ggc act gag gac tca ggc      2506
Leu Cys Leu Pro Gln Ile Glu Asn Val Lys Gly Thr Glu Asp Ser Gly
    725                 730                 735 acc aca gtg ctg ttg ccc ctg gtc att ttc ttt ggt ctt tgc ctt tta      2554
Thr Thr Val Leu Leu Pro Leu Val Ile Phe Phe Gly Leu Cys Leu Leu
740                 745                 750                 755 tcc ctc ctc ttc att ggt tta atg tat cgc tac caa cgg tgg aag tcc      2602
Ser Leu Leu Phe Ile Gly Leu Met Tyr Arg Tyr Gln Arg Trp Lys Ser
            760                 765                 770 aag ctc tac tcc att gtt tgt ggg aaa tcg aca cct gaa aaa gag ggg      2650
Lys Leu Tyr Ser Ile Val Cys Gly Lys Ser Thr Pro Glu Lys Glu Gly
            775                 780                 785 gag ctt gaa gga act act act aag ccc ctg gcc cca aac cca agc ttc      2698
Glu Leu Glu Gly Thr Thr Thr Lys Pro Leu Ala Pro Asn Pro Ser Phe
    790                 795                 800 agt ccc act cca ggc ttc acc ccc acc ctg ggc ttc agt ccc gtg ccc      2746
Ser Pro Thr Pro Gly Phe Thr Pro Thr Leu Gly Phe Ser Pro Val Pro
            805                 810                 815 agt tcc acc ttc acc tcc agc tcc acc tat acc ccc ggt gac tgt ccc      2794
Ser Ser Thr Phe Thr Ser Ser Ser Thr Tyr Thr Pro Gly Asp Cys Pro
820                 825                 830                 835
```

```
aac ttt gcg gct ccc cgc aga gag gtg gca cca ccc tat cag ggg gct    2842
Asn Phe Ala Ala Pro Arg Arg Glu Val Ala Pro Pro Tyr Gln Gly Ala
                840                 845                 850 gac ccc atc ctt gcg aca gcc ctc gcc tcc gac ccc atc ccc aac ccc    2890
Asp Pro Ile Leu Ala Thr Ala Leu Ala Ser Asp Pro Ile Pro Asn Pro
            855                 860                 865 ctt cag aag tgg gag gac agc gcc cac aag cca cag agc cta gac act    2938
Leu Gln Lys Trp Glu Asp Ser Ala His Lys Pro Gln Ser Leu Asp Thr
        870                 875                 880 gat gac ccc gcg acg ctg tac gcc gtg gtg gag aac gtg ccc ccg ttg    2986
Asp Asp Pro Ala Thr Leu Tyr Ala Val Val Glu Asn Val Pro Pro Leu
    885                 890                 895 cgc tgg aag gaa ttc gtg cgg cgc cta ggg ctg agc gac cac gag atc    3034
Arg Trp Lys Glu Phe Val Arg Arg Leu Gly Leu Ser Asp His Glu Ile
900                 905                 910                 915 gat cgg ctg gag ctg cag aac ggg cgc tgc ctg cgc gag gcg caa tac    3082
Asp Arg Leu Glu Leu Gln Asn Gly Arg Cys Leu Arg Glu Ala Gln Tyr
                920                 925                 930 agc atg ctg gcg acc tgg agg cgg cgc acg ccg cgg cgc gag gcc acg    3130
Ser Met Leu Ala Thr Trp Arg Arg Arg Thr Pro Arg Arg Glu Ala Thr
            935                 940                 945 ctg gag ctg ctg gga cgc gtg ctc cgc gac atg gac ctg ctg ggc tgc    3178
Leu Glu Leu Leu Gly Arg Val Leu Arg Asp Met Asp Leu Leu Gly Cys
        950                 955                 960 ctg gag gac atc gag gag gcg ctt tgc ggc ccc gcc gcc ctc ccg ccc    3226
Leu Glu Asp Ile Glu Glu Ala Leu Cys Gly Pro Ala Ala Leu Pro Pro
    965                 970                 975 gcg ccc agt ctt ctc aga tga ggctgcgccc ctgcgggcag ctctaaggac       3277
Ala Pro Ser Leu Leu Arg
980                 985 cgtcctgcga gatcgccttc caaccccact tttttctgga aaggaggggt cctgcagggg  3337
caagcaggag ctagcagccg cctacttggt gctaaccccct cgatgtacat agcttttctc 3397 agctgcctgc gcgccgccga cagtcagcgc tgtgcgcgcg gagagaggtg cgccgtgggc  3457
tcaagagcct gagtgggtgg tttgcgagga tgagggacgc tatgcctcat gcccgttttg  3517
ggtgtcctca ccagcaaggc tgctcggggg ccctggttc gtccctgagc cttttcaca   3577 gtgcataagc agttttttt gttttgtttt tgtttgttt tgtttttaaa tcaatcatgt   3637
tacactaata gaaacttggc actcctgtgc cctctgcctg acaagcaca tagcaagctg  3697 aactgtccta aggcaggggc gagcacggaa caatggggcc ttcagctgga gctgtggact  3757
tttgtacata cactaaaatt ctgaagttaa agctctgctc ttggaaaaaa aaaaaaaaa  3817 aaaaaaaaaa aaaaaaa                                                 3834

<210> SEQ ID NO 4
<211> LENGTH: 985
<212> TYPE: PRT
<213> ORGANISM: Homo sapiens

<400> SEQUENCE: 4

Met Glu Gly Asn Lys Leu Glu Glu Gln Asp Ser Ser Pro Pro Gln Ser
1               5                   10                  15

Thr Pro Gly Leu Met Lys Gly Asn Lys Arg Glu Glu Gln Gly Leu Gly
            20                  25                  30

Pro Glu Pro Ala Ala Pro Gln Gln Pro Thr Ala Glu Glu Glu Ala Leu
        35                  40                  45

Ile Glu Phe His Arg Ser Tyr Arg Glu Leu Phe Glu Phe Phe Cys Asn
    50                  55                  60
```

```
Asn Thr Thr Ile His Gly Ala Ile Arg Leu Val Cys Ser Gln His Asn
 65                  70                  75                  80

Arg Met Lys Thr Ala Phe Trp Ala Val Leu Trp Leu Cys Thr Phe Gly
                 85                  90                  95

Met Met Tyr Trp Gln Phe Gly Leu Leu Phe Gly Glu Tyr Phe Ser Tyr
            100                 105                 110

Pro Val Ser Leu Asn Ile Asn Leu Asn Ser Asp Lys Leu Val Phe Pro
            115                 120                 125

Ala Val Thr Ile Cys Thr Leu Asn Pro Tyr Arg Tyr Pro Glu Ile Lys
        130                 135                 140

Glu Glu Leu Glu Glu Leu Asp Arg Ile Thr Glu Gln Thr Leu Phe Asp
145                 150                 155                 160

Leu Tyr Lys Tyr Ser Ser Phe Thr Thr Leu Val Ala Gly Ser Arg Ser
                165                 170                 175

Arg Arg Asp Leu Arg Gly Thr Leu Pro His Pro Leu Gln Arg Leu Arg
            180                 185                 190

Val Pro Pro Pro His Gly Ala Arg Arg Ala Arg Ser Val Ala Ser
        195                 200                 205

Ser Leu Arg Asp Asn Asn Pro Gln Val Asp Trp Lys Asp Trp Lys Ile
210                 215                 220

Gly Phe Gln Leu Cys Asn Gln Asn Lys Ser Asp Cys Phe Tyr Gln Thr
225                 230                 235                 240

Tyr Ser Ser Gly Val Asp Ala Val Arg Glu Trp Tyr Arg Phe His Tyr
                245                 250                 255

Ile Asn Ile Leu Ser Arg Leu Pro Glu Thr Leu Pro Ser Leu Glu Glu
            260                 265                 270

Asp Thr Leu Gly Asn Phe Ile Phe Ala Cys Arg Phe Asn Gln Val Ser
        275                 280                 285

Cys Asn Gln Ala Asn Tyr Ser His Phe His His Pro Met Tyr Gly Asn
290                 295                 300

Cys Tyr Thr Phe Asn Asp Lys Asn Asn Ser Asn Leu Trp Met Ser Ser
305                 310                 315                 320

Met Pro Gly Ile Asn Asn Gly Leu Ser Leu Met Leu Arg Ala Glu Gln
                325                 330                 335

Asn Asp Phe Ile Pro Leu Leu Ser Thr Val Thr Gly Ala Arg Val Met
            340                 345                 350

Val His Gly Gln Asp Glu Pro Ala Phe Met Asp Asp Gly Gly Phe Asn
        355                 360                 365

Leu Arg Pro Gly Val Glu Thr Ser Ile Ser Met Arg Lys Glu Thr Leu
370                 375                 380

Asp Arg Leu Gly Gly Asp Tyr Gly Asp Cys Thr Lys Asn Gly Ser Asp
385                 390                 395                 400

Val Pro Val Glu Asn Leu Tyr Pro Ser Lys Tyr Thr Gln Gln Val Cys
                405                 410                 415

Ile His Ser Cys Phe Gln Glu Ser Met Ile Lys Glu Cys Gly Cys Ala
            420                 425                 430

Tyr Ile Phe Tyr Pro Arg Pro Gln Asn Val Glu Tyr Cys Asp Tyr Arg
        435                 440                 445

Lys His Ser Ser Trp Gly Tyr Cys Tyr Tyr Lys Leu Gln Val Asp Phe
        450                 455                 460

Ser Ser Asp His Leu Gly Cys Phe Thr Lys Cys Arg Lys Pro Cys Ser
465                 470                 475                 480

Val Thr Ser Tyr Gln Leu Ser Ala Gly Tyr Ser Arg Trp Pro Ser Val
```

```
                    485                 490                 495
Thr Ser Gln Glu Trp Val Phe Gln Met Leu Ser Arg Gln Asn Asn Tyr
            500                 505                 510
Thr Val Asn Asn Lys Arg Asn Gly Val Ala Lys Val Asn Ile Phe Phe
            515                 520                 525
Lys Glu Leu Asn Tyr Lys Thr Asn Ser Glu Ser Pro Ser Val Thr Val
            530                 535                 540
Leu Leu Glu Leu Leu Val Gly Ile Tyr Pro Ser Gly Val Ile Gly Leu
545                 550                 555                 560
Val Pro His Leu Gly Asp Arg Glu Lys Arg Asp Ser Val Cys Pro Gln
                565                 570                 575
Gly Lys Tyr Ile His Pro Gln Asn Asn Ser Ile Cys Cys Thr Lys Cys
            580                 585                 590
His Lys Gly Thr Tyr Leu Tyr Asn Asp Cys Pro Gly Pro Gly Gln Asp
            595                 600                 605
Thr Asp Cys Arg Glu Cys Glu Ser Gly Ser Phe Thr Ala Ser Glu Asn
            610                 615                 620
His Leu Arg His Cys Leu Ser Cys Ser Lys Cys Arg Lys Glu Met Gly
625                 630                 635                 640
Gln Val Glu Ile Ser Ser Cys Thr Val Asp Arg Asp Thr Val Cys Gly
                645                 650                 655
Cys Arg Lys Asn Gln Tyr Arg His Tyr Trp Ser Glu Asn Leu Phe Gln
            660                 665                 670
Cys Phe Asn Cys Ser Leu Cys Leu Asn Gly Thr Val His Leu Ser Cys
            675                 680                 685
Gln Glu Lys Gln Asn Thr Val Cys Thr Cys His Ala Gly Phe Phe Leu
            690                 695                 700
Arg Glu Asn Glu Cys Val Ser Cys Ser Asn Cys Lys Lys Ser Leu Glu
705                 710                 715                 720
Cys Thr Lys Leu Cys Leu Pro Gln Ile Glu Asn Val Lys Gly Thr Glu
                725                 730                 735
Asp Ser Gly Thr Thr Val Leu Leu Pro Leu Val Ile Phe Phe Gly Leu
            740                 745                 750
Cys Leu Leu Ser Leu Leu Phe Ile Gly Leu Met Tyr Arg Tyr Gln Arg
            755                 760                 765
Trp Lys Ser Lys Leu Tyr Ser Ile Val Cys Gly Lys Ser Thr Pro Glu
            770                 775                 780
Lys Glu Gly Glu Leu Glu Gly Thr Thr Thr Lys Pro Leu Ala Pro Asn
785                 790                 795                 800
Pro Ser Phe Ser Pro Thr Pro Gly Phe Thr Pro Thr Leu Gly Phe Ser
                805                 810                 815
Pro Val Pro Ser Ser Thr Phe Thr Ser Ser Ser Thr Tyr Thr Pro Gly
            820                 825                 830
Asp Cys Pro Asn Phe Ala Ala Pro Arg Arg Glu Val Ala Pro Pro Tyr
            835                 840                 845
Gln Gly Ala Asp Pro Ile Leu Ala Thr Ala Leu Ala Ser Asp Pro Ile
850                 855                 860
Pro Asn Pro Leu Gln Lys Trp Glu Asp Ser Ala His Lys Pro Gln Ser
865                 870                 875                 880
Leu Asp Thr Asp Asp Pro Ala Thr Leu Tyr Ala Val Val Glu Asn Val
                885                 890                 895
Pro Pro Leu Arg Trp Lys Glu Phe Val Arg Arg Leu Gly Leu Ser Asp
            900                 905                 910
```

```
His Glu Ile Asp Arg Leu Glu Leu Gln Asn Gly Arg Cys Leu Arg Glu
            915                 920                 925

Ala Gln Tyr Ser Met Leu Ala Thr Trp Arg Arg Thr Pro Arg Arg
        930                 935                 940

Glu Ala Thr Leu Glu Leu Leu Gly Arg Val Leu Arg Asp Met Asp Leu
945                 950                 955                 960

Leu Gly Cys Leu Glu Asp Ile Glu Glu Ala Leu Cys Gly Pro Ala Ala
                965                 970                 975

Leu Pro Pro Ala Pro Ser Leu Leu Arg
            980                 985

<210> SEQ ID NO 5
<211> LENGTH: 4017
<212> TYPE: DNA
<213> ORGANISM: Homo sapiens
<220> FEATURE:
<221> NAME/KEY: CDS
<222> LOCATION: (290)..(3430)

<400> SEQUENCE: 5
```

| | | |
|---|---|---|
| cttgcctgtc tgcgtctaaa gcccctgccc agagtccgcc ttctcaggtc cagtactccc | 60 |
| agttcacctg ccctcgggag ccctccttcc ttcggaaaac tcccggctct gactcctcct | 120 |
| cagcccctcc ccccgccctg ctcacccttta attgagatgc taatgagatt cctgtcgctt | 180 |
| ccatccctgg ccggccagcg gcgggctccc cagccaggc cgctgcacct gtcaggggaa | 240 |
| caagctggag gagcaggacc ctagacctct gcagcccata ccaggtctc atg gag ggg | 298 |
|  | Met Glu Gly |
|  | 1 |

```
aac aag ctg gag gag cag gac tct agc cct cca cag tcc act cca ggg      346
Asn Lys Leu Glu Glu Gln Asp Ser Ser Pro Pro Gln Ser Thr Pro Gly
  5                  10                  15 ctc atg aag ggg aac aag cgt gag gag cag ggg ctg ggc ccc gaa cct      394
Leu Met Lys Gly Asn Lys Arg Glu Glu Gln Gly Leu Gly Pro Glu Pro
 20                  25                  30                  35 gcg gcg ccc cag cag ccc acg gcg gag gag gag gcc ctg atc gag ttc      442
Ala Ala Pro Gln Gln Pro Thr Ala Glu Glu Glu Ala Leu Ile Glu Phe
                 40                  45                  50 cac cgc tcc tac cga gag ctc ttc gag ttc ttc tgc aac aac acc acc      490
His Arg Ser Tyr Arg Glu Leu Phe Glu Phe Phe Cys Asn Asn Thr Thr
         55                  60                  65 atc cac ggc gcc atc cgc ctg gtg tgc tcc cag cac aac cgc atg aag      538
Ile His Gly Ala Ile Arg Leu Val Cys Ser Gln His Asn Arg Met Lys
     70                  75                  80 acg gcc ttc tgg gca gtg ctg tgg ctc tgc acc ttt ggc atg atg tac      586
Thr Ala Phe Trp Ala Val Leu Trp Leu Cys Thr Phe Gly Met Met Tyr
 85                  90                  95 tgg caa ttc ggc ctg ctt ttc gga gag tac ttc agc tac ccc gtc agc      634
Trp Gln Phe Gly Leu Leu Phe Gly Glu Tyr Phe Ser Tyr Pro Val Ser
100                 105                 110                 115 ctc aac atc aac ctc aac tcg gac aag ctc gtc ttc ccc gca gtg acc      682
Leu Asn Ile Asn Leu Asn Ser Asp Lys Leu Val Phe Pro Ala Val Thr
                120                 125                 130 atc tgc acc ctc aat ccc tac agg tac ccg gaa att aaa gag gag ctg      730
Ile Cys Thr Leu Asn Pro Tyr Arg Tyr Pro Glu Ile Lys Glu Glu Leu
        135                 140                 145 gag gag ctg gac cgc atc aca gag cag acg ctc ttt gac ctg tac aaa      778
Glu Glu Leu Asp Arg Ile Thr Glu Gln Thr Leu Phe Asp Leu Tyr Lys
    150                 155                 160 tac agc tcc ttc acc act ctc gtg gcc ggc tcc cgc agc cgt cgc gac      826
Tyr Ser Ser Phe Thr Thr Leu Val Ala Gly Ser Arg Ser Arg Arg Asp
```

```
                165                 170                 175
ctg cgg ggg act ctg ccg cac ccc ttg cag cgc ctg agg gtc ccg ccc        874
Leu Arg Gly Thr Leu Pro His Pro Leu Gln Arg Leu Arg Val Pro Pro
180                 185                 190                 195 ccg cct cac ggg gcc cgt cga gcc cgt agc gtg gcc tcc agc ttg cgg        922
Pro Pro His Gly Ala Arg Arg Ala Arg Ser Val Ala Ser Ser Leu Arg
                200                 205                 210 gac aac aac ccc cag gtg gac tgg aag gac tgg aag atc ggc ttc cag        970
Asp Asn Asn Pro Gln Val Asp Trp Lys Asp Trp Lys Ile Gly Phe Gln
            215                 220                 225 ctg tgc aac cag aac aaa tcg gac tgc ttc tac cag aca tac tca tca       1018
Leu Cys Asn Gln Asn Lys Ser Asp Cys Phe Tyr Gln Thr Tyr Ser Ser
        230                 235                 240 ggg gtg gat gcg gtg agg gag tgg tac cgc ttc cac tac atc aac atc       1066
Gly Val Asp Ala Val Arg Glu Trp Tyr Arg Phe His Tyr Ile Asn Ile
    245                 250                 255 ctg tcg agg ctg cca gag act ctg cca tcc ctg gag gag gac acg ctg       1114
Leu Ser Arg Leu Pro Glu Thr Leu Pro Ser Leu Glu Glu Asp Thr Leu
260                 265                 270                 275 ggc aac ttc atc ttc gcc tgc cgc ttc aac cag gtc tcc tgc aac cag       1162
Gly Asn Phe Ile Phe Ala Cys Arg Phe Asn Gln Val Ser Cys Asn Gln
                280                 285                 290 gcg aat tac tct cac ttc cac cac ccg atg tat gga aac tgc tat act       1210
Ala Asn Tyr Ser His Phe His His Pro Met Tyr Gly Asn Cys Tyr Thr
            295                 300                 305 ttc aat gac aag aac aac tcc aac ctc tgg atg tct tcc atg cct gga       1258
Phe Asn Asp Lys Asn Asn Ser Asn Leu Trp Met Ser Ser Met Pro Gly
        310                 315                 320 atc aac aac ggt ctg tcc ctg atg ctg cgc gca gag cag aat gac ttc       1306
Ile Asn Asn Gly Leu Ser Leu Met Leu Arg Ala Glu Gln Asn Asp Phe
    325                 330                 335 att ccc ctg ctg tcc aca gtg act ggg gcc cgg gta atg gtg cac ggg       1354
Ile Pro Leu Leu Ser Thr Val Thr Gly Ala Arg Val Met Val His Gly
340                 345                 350                 355 cag gat gaa cct gcc ttt atg gat gat ggt ggc ttt aac ttg cgg cct       1402
Gln Asp Glu Pro Ala Phe Met Asp Asp Gly Gly Phe Asn Leu Arg Pro
                360                 365                 370 ggc gtg gag acc tcc atc agc atg agg aag gaa acc ctg gac aga ctt       1450
Gly Val Glu Thr Ser Ile Ser Met Arg Lys Glu Thr Leu Asp Arg Leu
            375                 380                 385 ggg ggc gat tat ggc gac tgc acc aag aat ggc agt gat gtt cct gtt       1498
Gly Gly Asp Tyr Gly Asp Cys Thr Lys Asn Gly Ser Asp Val Pro Val
        390                 395                 400 gag aac ctt tac cct tca aag tac aca cag cag gtg tgt att cac tcc       1546
Glu Asn Leu Tyr Pro Ser Lys Tyr Thr Gln Gln Val Cys Ile His Ser
    405                 410                 415 tgc ttc cag gag agc atg atc aag gag tgt ggc tgt gcc tac atc ttc       1594
Cys Phe Gln Glu Ser Met Ile Lys Glu Cys Gly Cys Ala Tyr Ile Phe
420                 425                 430                 435 tat ccg cgg ccc cag aac gtg gag tac tgt gac tac aga aag cac agt       1642
Tyr Pro Arg Pro Gln Asn Val Glu Tyr Cys Asp Tyr Arg Lys His Ser
                440                 445                 450 tcc tgg ggg tac tgc tac tat aag ctc cag gtt gac ttc tcc tca gac       1690
Ser Trp Gly Tyr Cys Tyr Tyr Lys Leu Gln Val Asp Phe Ser Ser Asp
            455                 460                 465 cac ctg ggc tgt ttc acc aag tgc cgg aag cca tgc agc gtg acc agc       1738
His Leu Gly Cys Phe Thr Lys Cys Arg Lys Pro Cys Ser Val Thr Ser
        470                 475                 480 tac cag ctc tct gct ggt tac tca cga tgg ccc tcg gtg aca tcc cag       1786
Tyr Gln Leu Ser Ala Gly Tyr Ser Arg Trp Pro Ser Val Thr Ser Gln
```

```
                485                 490                 495
gaa tgg gtc ttc cag atg cta tcg cga cag aac aat tac acc gtc aac    1834
Glu Trp Val Phe Gln Met Leu Ser Arg Gln Asn Asn Tyr Thr Val Asn
500                 505                 510                 515 aac aag aga aat gga gtg gcc aaa gtc aac atc ttc ttc aag gag ctg    1882
Asn Lys Arg Asn Gly Val Ala Lys Val Asn Ile Phe Phe Lys Glu Leu
                520                 525                 530 aac tac aaa acc aat tct gag tct ccc tct gtc acg atg gtc acc ctc    1930
Asn Tyr Lys Thr Asn Ser Glu Ser Pro Ser Val Thr Met Val Thr Leu
            535                 540                 545 ctg tcc aac ctg ggc agc cag tgg agc ctg tgg ttc ggc tcc tcg gtg    1978
Leu Ser Asn Leu Gly Ser Gln Trp Ser Leu Trp Phe Gly Ser Ser Val
        550                 555                 560 ttg tct gtg gtg gag atg gct gag ctc gtc ttt gac ctg ctg gtc atc    2026
Leu Ser Val Val Glu Met Ala Glu Leu Val Phe Asp Leu Leu Val Ile
565                 570                 575 atg ttc ctc atg ctg ctc cga agg ttc cga agc cga tac tgg tct cca    2074
Met Phe Leu Met Leu Leu Arg Arg Phe Arg Ser Arg Tyr Trp Ser Pro
580                 585                 590                 595 ggc cga ggg ggc agg ggt gct cag gag gtg ctc ctg gag ctg ttg gtg    2122
Gly Arg Gly Gly Arg Gly Ala Gln Glu Val Leu Leu Glu Leu Leu Val
                600                 605                 610 gga ata tac ccc tca ggg gtt att gga ctg gtc cct cac cta ggg gac    2170
Gly Ile Tyr Pro Ser Gly Val Ile Gly Leu Val Pro His Leu Gly Asp
            615                 620                 625 agg gag aag aga gat agt gtg tgt ccc caa gga aaa tat atc cac cct    2218
Arg Glu Lys Arg Asp Ser Val Cys Pro Gln Gly Lys Tyr Ile His Pro
        630                 635                 640 caa aat aat tcg att tgc tgt acc aag tgc cac aaa gga acc tac ttg    2266
Gln Asn Asn Ser Ile Cys Cys Thr Lys Cys His Lys Gly Thr Tyr Leu
645                 650                 655 tac aat gac tgt cca ggc ccg ggg cag gat acg gac tgc agg gag tgt    2314
Tyr Asn Asp Cys Pro Gly Pro Gly Gln Asp Thr Asp Cys Arg Glu Cys
660                 665                 670                 675 gag agc ggc tcc ttc acc gct tca gaa aac cac ctc aga cac tgc ctc    2362
Glu Ser Gly Ser Phe Thr Ala Ser Glu Asn His Leu Arg His Cys Leu
                680                 685                 690 agc tgc tcc aaa tgc cga aag gaa atg ggt cag gtg gag atc tct tct    2410
Ser Cys Ser Lys Cys Arg Lys Glu Met Gly Gln Val Glu Ile Ser Ser
            695                 700                 705 tgc aca gtg gac cgg gac acc gtg tgt ggc tgc agg aag aac cag tac    2458
Cys Thr Val Asp Arg Asp Thr Val Cys Gly Cys Arg Lys Asn Gln Tyr
        710                 715                 720 cgg cat tat tgg agt gaa aac ctt ttc cag tgc ttc aat tgc agc ctc    2506
Arg His Tyr Trp Ser Glu Asn Leu Phe Gln Cys Phe Asn Cys Ser Leu
725                 730                 735 tgc ctc aat ggg acc gtg cac ctc tcc tgc cag gag aaa cag aac acc    2554
Cys Leu Asn Gly Thr Val His Leu Ser Cys Gln Glu Lys Gln Asn Thr
740                 745                 750                 755 gtg tgc acc tgc cat gca ggt ttc ttt cta aga gaa aac gag tgt gtc    2602
Val Cys Thr Cys His Ala Gly Phe Phe Leu Arg Glu Asn Glu Cys Val
                760                 765                 770 tcc tgt agt aac tgt aag aaa agc ctg gag tgc acg aag ttg tgc cta    2650
Ser Cys Ser Asn Cys Lys Lys Ser Leu Glu Cys Thr Lys Leu Cys Leu
            775                 780                 785 ccc cag att gag aat gtt aag ggc act gag gac tca ggc acc aca gtg    2698
Pro Gln Ile Glu Asn Val Lys Gly Thr Glu Asp Ser Gly Thr Thr Val
        790                 795                 800 ctg ttg ccc ctg gtc att ttc ttt ggt ctt tgc ctt tta tcc ctc ctc    2746
Leu Leu Pro Leu Val Ile Phe Phe Gly Leu Cys Leu Leu Ser Leu Leu
```

```
                     805                 810                 815
ttc att ggt tta atg tat cgc tac caa cgg tgg aag tcc aag ctc tac       2794
Phe Ile Gly Leu Met Tyr Arg Tyr Gln Arg Trp Lys Ser Lys Leu Tyr
820                 825                 830                 835 tcc att gtt tgt ggg aaa tcg aca cct gaa aaa gag ggg gag ctt gaa       2842
Ser Ile Val Cys Gly Lys Ser Thr Pro Glu Lys Glu Gly Glu Leu Glu
                840                 845                 850 gga act act act aag ccc ctg gcc cca aac cca agc ttc agt ccc act       2890
Gly Thr Thr Thr Lys Pro Leu Ala Pro Asn Pro Ser Phe Ser Pro Thr
            855                 860                 865 cca ggc ttc acc ccc acc ctg ggc ttc agt ccc gtg ccc agt tcc acc       2938
Pro Gly Phe Thr Pro Thr Leu Gly Phe Ser Pro Val Pro Ser Ser Thr
        870                 875                 880 ttc acc tcc agc tcc acc tat acc ccc ggt gac tgt ccc aac ttt gcg       2986
Phe Thr Ser Ser Ser Thr Tyr Thr Pro Gly Asp Cys Pro Asn Phe Ala
    885                 890                 895 gct ccc cgc aga gag gtg gca cca ccc tat cag ggg gct gac ccc atc       3034
Ala Pro Arg Arg Glu Val Ala Pro Pro Tyr Gln Gly Ala Asp Pro Ile
900                 905                 910                 915 ctt gcg aca gcc ctc gcc tcc gac ccc atc ccc aac ccc ctt cag aag       3082
Leu Ala Thr Ala Leu Ala Ser Asp Pro Ile Pro Asn Pro Leu Gln Lys
                920                 925                 930 tgg gag gac agc gcc cac aag cca cag agc cta gac act gat gac ccc       3130
Trp Glu Asp Ser Ala His Lys Pro Gln Ser Leu Asp Thr Asp Asp Pro
            935                 940                 945 gcg acg ctg tac gcc gtg gtg gag aac gtg ccc ccg ttg cgc tgg aag       3178
Ala Thr Leu Tyr Ala Val Val Glu Asn Val Pro Pro Leu Arg Trp Lys
        950                 955                 960 gaa ttc gtg cgg cgc cta ggg ctg agc gac cac gag atc gat cgg ctg       3226
Glu Phe Val Arg Arg Leu Gly Leu Ser Asp His Glu Ile Asp Arg Leu
    965                 970                 975 gag ctg cag aac ggg cgc tgc ctg cgc gag gcg caa tac agc atg ctg       3274
Glu Leu Gln Asn Gly Arg Cys Leu Arg Glu Ala Gln Tyr Ser Met Leu
980                 985                 990                 995 gcg acc tgg agg cgg  cgc acg ccg cgg cgc  gag gcc acg ctg gag         3319
Ala Thr Trp Arg Arg  Arg Thr Pro Arg Arg  Glu Ala Thr Leu Glu
                1000                1005                1010 ctg ctg gga cgc gtg  ctc cgc gac atg gac  ctg ctg ggc tgc ctg         3364
Leu Leu Gly Arg Val  Leu Arg Asp Met Asp  Leu Leu Gly Cys Leu
                1015                1020                1025 gag gac atc gag gag  gcg ctt tgc ggc ccc  gcc gcc ctc ccg ccc         3409
Glu Asp Ile Glu Glu  Ala Leu Cys Gly Pro  Ala Ala Leu Pro Pro
                1030                1035                1040 gcg ccc agt ctt ctc aga tga ggctgcgccc ctgcgggcag ctctaaggac          3460
Ala Pro Ser Leu Leu Arg
                1045 cgtcctgcga gatcgccttc caaccccact tttttctgga aaggaggggt cctgcagggg     3520 caagcaggag ctagcagccg cctacttggt gctaacccct cgatgtacat agcttttctc     3580 agctgcctgc gcgccgccga cagtcagcgc tgtgcgcgcg gagagaggtg cgccgtgggc     3640 tcaagagcct gagtggtgg tttgcgagga tgagggacgc tatgcctcat gcccgttttg      3700 ggtgtcctca ccagcaaggc tgctcggggg cccctggttc gtccctgagc cttttcaca     3760 gtgcataagc agttttttt gttttgtttt tgttttgttt tgttttttaaa tcaatcatgt     3820 tacactaata gaaacttggc actcctgtgc cctctgcctg gacaagcaca tagcaagctg     3880 aactgtccta aggcagggc gagcacggaa caatggggcc ttcagctgga gctgtggact      3940 tttgtacata cactaaaatt ctgaagttaa agctctgctc ttggaaaaaa aaaaaaaaaa     4000
```
aaaaaaaaaa aaaaaa 4017

<210> SEQ ID NO 6
<211> LENGTH: 1046
<212> TYPE: PRT
<213> ORGANISM: Homo sapiens

<400> SEQUENCE: 6

Met Glu Gly Asn Lys Leu Glu Glu Gln Asp Ser Ser Pro Pro Gln Ser
1               5                   10                  15

Thr Pro Gly Leu Met Lys Gly Asn Lys Arg Glu Glu Gln Gly Leu Gly
            20                  25                  30

Pro Glu Pro Ala Ala Pro Gln Pro Thr Ala Glu Glu Ala Leu
        35                  40                  45

Ile Glu Phe His Arg Ser Tyr Arg Glu Leu Phe Glu Phe Phe Cys Asn
    50                  55                  60

Asn Thr Thr Ile His Gly Ala Ile Arg Leu Val Cys Ser Gln His Asn
65                  70                  75                  80

Arg Met Lys Thr Ala Phe Trp Ala Val Leu Trp Leu Cys Thr Phe Gly
                85                  90                  95

Met Met Tyr Trp Gln Phe Gly Leu Leu Phe Gly Glu Tyr Phe Ser Tyr
            100                 105                 110

Pro Val Ser Leu Asn Ile Asn Leu Asn Ser Asp Lys Leu Val Phe Pro
        115                 120                 125

Ala Val Thr Ile Cys Thr Leu Asn Pro Tyr Arg Tyr Pro Glu Ile Lys
    130                 135                 140

Glu Glu Leu Glu Glu Leu Asp Arg Ile Thr Glu Gln Thr Leu Phe Asp
145                 150                 155                 160

Leu Tyr Lys Tyr Ser Ser Phe Thr Thr Leu Val Ala Gly Ser Arg Ser
                165                 170                 175

Arg Arg Asp Leu Arg Gly Thr Leu Pro His Pro Leu Gln Arg Leu Arg
            180                 185                 190

Val Pro Pro Pro His Gly Ala Arg Arg Ala Arg Ser Val Ala Ser
        195                 200                 205

Ser Leu Arg Asp Asn Asn Pro Gln Val Asp Trp Lys Asp Trp Lys Ile
    210                 215                 220

Gly Phe Gln Leu Cys Asn Gln Asn Lys Ser Asp Cys Phe Tyr Gln Thr
225                 230                 235                 240

Tyr Ser Ser Gly Val Asp Ala Val Arg Glu Trp Tyr Arg Phe His Tyr
                245                 250                 255

Ile Asn Ile Leu Ser Arg Leu Pro Glu Thr Leu Pro Ser Leu Glu Glu
            260                 265                 270

Asp Thr Leu Gly Asn Phe Ile Phe Ala Cys Arg Phe Asn Gln Val Ser
        275                 280                 285

Cys Asn Gln Ala Asn Tyr Ser His Phe His His Pro Met Tyr Gly Asn
    290                 295                 300

Cys Tyr Thr Phe Asn Asp Lys Asn Asn Ser Asn Leu Trp Met Ser Ser
305                 310                 315                 320

Met Pro Gly Ile Asn Asn Gly Leu Ser Leu Met Leu Arg Ala Glu Gln
                325                 330                 335

Asn Asp Phe Ile Pro Leu Leu Ser Thr Val Thr Gly Ala Arg Val Met
            340                 345                 350

Val His Gly Gln Asp Glu Pro Ala Phe Met Asp Asp Gly Gly Phe Asn
        355                 360                 365

Leu Arg Pro Gly Val Glu Thr Ser Ile Ser Met Arg Lys Glu Thr Leu

```
                370             375             380
Asp Arg Leu Gly Gly Asp Tyr Gly Asp Cys Thr Lys Asn Gly Ser Asp
385             390             395             400

Val Pro Val Glu Asn Leu Tyr Pro Ser Lys Tyr Thr Gln Gln Val Cys
            405             410             415

Ile His Ser Cys Phe Gln Glu Ser Met Ile Lys Glu Cys Gly Cys Ala
            420             425             430

Tyr Ile Phe Tyr Pro Arg Pro Gln Asn Val Glu Tyr Cys Asp Tyr Arg
            435             440             445

Lys His Ser Ser Trp Gly Tyr Cys Tyr Tyr Lys Leu Gln Val Asp Phe
            450             455             460

Ser Ser Asp His Leu Gly Cys Phe Thr Lys Cys Arg Lys Pro Cys Ser
465             470             475             480

Val Thr Ser Tyr Gln Leu Ser Ala Gly Tyr Ser Arg Trp Pro Ser Val
            485             490             495

Thr Ser Gln Glu Trp Val Phe Gln Met Leu Ser Arg Gln Asn Asn Tyr
            500             505             510

Thr Val Asn Asn Lys Arg Asn Gly Val Ala Lys Val Asn Ile Phe Phe
            515             520             525

Lys Glu Leu Asn Tyr Lys Thr Asn Ser Glu Ser Pro Ser Val Thr Met
            530             535             540

Val Thr Leu Leu Ser Asn Leu Gly Ser Gln Trp Ser Leu Trp Phe Gly
545             550             555             560

Ser Ser Val Leu Ser Val Val Glu Met Ala Glu Leu Val Phe Asp Leu
            565             570             575

Leu Val Ile Met Phe Leu Met Leu Leu Arg Arg Phe Arg Ser Arg Tyr
            580             585             590

Trp Ser Pro Gly Arg Gly Gly Arg Gly Ala Gln Glu Val Leu Leu Glu
            595             600             605

Leu Leu Val Gly Ile Tyr Pro Ser Gly Val Ile Gly Leu Val Pro His
            610             615             620

Leu Gly Asp Arg Glu Lys Arg Asp Ser Val Cys Pro Gln Gly Lys Tyr
625             630             635             640

Ile His Pro Gln Asn Asn Ser Ile Cys Cys Thr Lys Cys His Lys Gly
            645             650             655

Thr Tyr Leu Tyr Asn Asp Cys Pro Gly Pro Gly Gln Asp Thr Asp Cys
            660             665             670

Arg Glu Cys Glu Ser Gly Ser Phe Thr Ala Ser Glu Asn His Leu Arg
            675             680             685

His Cys Leu Ser Cys Ser Lys Cys Arg Lys Glu Met Gly Gln Val Glu
            690             695             700

Ile Ser Ser Cys Thr Val Asp Arg Asp Thr Val Cys Gly Cys Arg Lys
705             710             715             720

Asn Gln Tyr Arg His Tyr Trp Ser Glu Asn Leu Phe Gln Cys Phe Asn
            725             730             735

Cys Ser Leu Cys Leu Asn Gly Thr Val His Leu Ser Cys Gln Glu Lys
            740             745             750

Gln Asn Thr Val Cys Thr Cys His Ala Gly Phe Phe Leu Arg Glu Asn
            755             760             765

Glu Cys Val Ser Cys Ser Asn Cys Lys Lys Ser Leu Glu Cys Thr Lys
            770             775             780

Leu Cys Leu Pro Gln Ile Glu Asn Val Lys Gly Thr Glu Asp Ser Gly
785             790             795             800
```

-continued

```
Thr Thr Val Leu Leu Pro Leu Val Ile Phe Phe Gly Leu Cys Leu Leu
            805                 810                 815

Ser Leu Leu Phe Ile Gly Leu Met Tyr Arg Tyr Gln Arg Trp Lys Ser
            820                 825                 830

Lys Leu Tyr Ser Ile Val Cys Gly Lys Ser Thr Pro Glu Lys Glu Gly
            835                 840                 845

Glu Leu Glu Gly Thr Thr Thr Lys Pro Leu Ala Pro Asn Pro Ser Phe
            850                 855                 860

Ser Pro Thr Pro Gly Phe Thr Pro Thr Leu Gly Phe Ser Pro Val Pro
865                 870                 875                 880

Ser Ser Thr Phe Thr Ser Ser Thr Tyr Thr Pro Gly Asp Cys Pro
            885                 890                 895

Asn Phe Ala Ala Pro Arg Arg Glu Val Ala Pro Pro Tyr Gln Gly Ala
            900                 905                 910

Asp Pro Ile Leu Ala Thr Ala Leu Ala Ser Asp Pro Ile Pro Asn Pro
            915                 920                 925

Leu Gln Lys Trp Glu Asp Ser Ala His Lys Pro Gln Ser Leu Asp Thr
            930                 935                 940

Asp Asp Pro Ala Thr Leu Tyr Ala Val Val Glu Asn Val Pro Pro Leu
945                 950                 955                 960

Arg Trp Lys Glu Phe Val Arg Arg Leu Gly Leu Ser Asp His Glu Ile
            965                 970                 975

Asp Arg Leu Glu Leu Gln Asn Gly Arg Cys Leu Arg Glu Ala Gln Tyr
            980                 985                 990

Ser Met Leu Ala Thr Trp Arg Arg  Arg Thr Pro Arg  Arg Glu Ala Thr
            995                 1000                1005

Leu Glu  Leu Leu Gly Arg Val  Leu Arg Asp Met Asp  Leu Leu Gly
    1010                1015                1020

Cys Leu  Glu Asp Ile Glu Glu  Ala Leu Cys Gly Pro  Ala Ala Leu
    1025                1030                1035

Pro Pro  Ala Pro Ser Leu Leu  Arg
    1040                1045

<210> SEQ ID NO 7
<211> LENGTH: 26
<212> TYPE: DNA
<213> ORGANISM: Artificial Sequence
<220> FEATURE:
<223> OTHER INFORMATION: primer

<400> SEQUENCE: 7
catcttcttc aaggagctga actaca                                       26

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
gaccagtcca ataacccctg ag                                           22

<210> SEQ ID NO 9
<211> LENGTH: 16
<212> TYPE: DNA
<213> ORGANISM: Artificial Sequence
<220> FEATURE:
<223> OTHER INFORMATION: probe
```

-continued

```
<400> SEQUENCE: 9
ctgtcacggt gctcct                                              16

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ccgaagccga tactggtctc                                          20

<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
gaccagtcca ataacccctg ag                                       22

<210> SEQ ID NO 12
<211> LENGTH: 16
<212> TYPE: DNA
<213> ORGANISM: Artificial Sequence
<220> FEATURE:
<223> OTHER INFORMATION: probe

<400> SEQUENCE: 12
ctcaggaggt gctcct                                              16

<210> SEQ ID NO 13
<211> LENGTH: 59
<212> TYPE: PRT
<213> ORGANISM: Homo sapiens

<400> SEQUENCE: 13

Met Gly Met Ala Arg Gly Ser Leu Thr Arg Val Pro Gly Val Met Gly
1               5                   10                  15

Glu Gly Thr Gln Gly Pro Glu Leu Ser Leu Asp Pro Asp Pro Cys Ser
            20                  25                  30

Pro Gln Ser Thr Pro Gly Leu Met Lys Gly Asn Lys Leu Glu Glu Gln
        35                  40                  45

Asp Pro Arg Pro Leu Gln Pro Ile Pro Gly Leu
    50                  55

<210> SEQ ID NO 14
<211> LENGTH: 23
<212> TYPE: PRT
<213> ORGANISM: Homo sapiens

<400> SEQUENCE: 14

Met Ser Ser Ile Lys Gly Asn Lys Leu Glu Glu Gln Asp Pro Arg Pro
1               5                   10                  15

Leu Gln Pro Ile Pro Gly Leu
            20
```